United States Patent
Alexander et al.

(10) Patent No.: US 10,653,411 B2
(45) Date of Patent: May 19, 2020

(54) IMPLANTS, TOOLS, AND METHODS FOR TREATMENTS OF PELVIC CONDITIONS

(71) Applicant: Boston Scientific Scimed, Inc., Maple Grove, MN (US)

(72) Inventors: James A. Alexander, Excelsior, MN (US); Chaouki A. Khamis, Cupertino, CA (US); Justin H. Huelman, Lino Lakes, MN (US); William S. Tremulis, Redwood City, CA (US); Thomas O. Viker, Arden Hills, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 251 days.

(21) Appl. No.: 15/155,516

(22) Filed: May 16, 2016

(65) Prior Publication Data

US 2016/0256151 A1    Sep. 8, 2016

Related U.S. Application Data

(62) Division of application No. 13/537,612, filed on Jun. 29, 2012, now Pat. No. 9,351,723.
(Continued)

(51) Int. Cl.
*A61B 17/04* (2006.01)
*A61B 17/062* (2006.01)
(Continued)

(52) U.S. Cl.
CPC ...... *A61B 17/0469* (2013.01); *A61B 17/0482* (2013.01); *A61B 17/0483* (2013.01);
(Continued)

(58) Field of Classification Search
CPC ............ A61B 17/0469; A61B 17/0482; A61B 17/0483; A61B 17/0625;
(Continued)

(56) References Cited

U.S. PATENT DOCUMENTS

| 2,738,790 A | 3/1956 | Todt et al. |
| 3,124,136 A | 3/1964 | Usher |

(Continued)

FOREIGN PATENT DOCUMENTS

| AU | 2002241673 | 11/2005 |
| CA | 2404459 | 8/2005 |

(Continued)

OTHER PUBLICATIONS

"Access Instrument System with AlloSling Fascia" (5 pages with two pages of Instructions for Use).
(Continued)

*Primary Examiner* — Katherine M Shi
(74) *Attorney, Agent, or Firm* — Brake Hughes Bellerman LLP (57) ABSTRACT

Described are various embodiments of surgical procedures, systems, implants, devices, tools, and methods, useful for treating pelvic conditions in a male or female, the pelvic conditions including incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness, the devices and tools including devices and tools for anchoring an implant to tissue.

4 Claims, 4 Drawing Sheets

Related U.S. Application Data (60) Provisional application No. 61/503,009, filed on Jun. 30, 2011, provisional application No. 61/506,833, filed on Jul. 12, 2011.

(51) Int. Cl.
*A61F 2/00* (2006.01)
*A61B 17/00* (2006.01)
*A61B 17/06* (2006.01)

(52) U.S. Cl.
CPC ........ *A61B 17/0625* (2013.01); *A61F 2/0045* (2013.01); *A61B 2017/00539* (2013.01); *A61B 2017/00544* (2013.01); *A61B 2017/00805* (2013.01); *A61B 2017/06042* (2013.01); *A61F 2002/0072* (2013.01)

(58) Field of Classification Search
CPC ........... A61B 2017/00805; A61B 2017/06042; A61B 17/0485; A61M 2005/3206; A61M 5/3296; A61M 5/250014; A61M 25/0097
USPC ........................ 606/139, 144–146
See application file for complete search history.

(56) References Cited

U.S. PATENT DOCUMENTS

| | | |
|---|---|---|
| 3,182,662 A | 5/1965 | Shirodkar |
| 3,311,110 A | 3/1967 | Singerman et al. |
| 3,384,073 A | 5/1968 | Van Winkle, Jr. |
| 3,472,232 A | 10/1969 | Earl |
| 3,580,313 A | 5/1971 | McKnight |
| 3,763,860 A | 10/1973 | Clarke |
| 3,789,828 A | 2/1974 | Schulte |
| 3,815,576 A | 6/1974 | Balaban |
| 3,858,783 A | 1/1975 | Kapitanov et al. |
| 3,924,633 A | 12/1975 | Cook et al. |
| 3,995,619 A | 12/1976 | Glatzer |
| 4,019,499 A | 4/1977 | Fitzgerald |
| 4,037,603 A | 7/1977 | Wendorff |
| 4,128,100 A | 12/1978 | Wendorff |
| 4,172,458 A | 10/1979 | Pereyra |
| 4,224,947 A * | 9/1980 | Fukuda .................. A61B 17/04 606/146 |
| 4,235,238 A | 11/1980 | Ogiu et al. |
| 4,246,660 A | 1/1981 | Wevers |
| 4,441,497 A | 4/1984 | Paudler |
| 4,509,516 A | 4/1985 | Richmond |
| 4,548,202 A | 10/1985 | Duncan |
| 4,632,100 A | 12/1986 | Somers et al. |
| 4,775,380 A | 10/1988 | Seedhom et al. |
| 4,857,041 A | 8/1989 | Annis et al. |
| 4,865,031 A | 9/1989 | O'Keeffe |
| 4,873,976 A | 10/1989 | Schreiber |
| 4,920,986 A | 5/1990 | Biswas |
| 4,932,962 A | 6/1990 | Yoon et al. |
| 4,938,760 A | 7/1990 | Burton et al. |
| 4,969,892 A | 11/1990 | Burton et al. |
| 5,007,894 A | 4/1991 | Enhorning |
| 5,012,822 A | 5/1991 | Schwarz |
| 5,013,292 A | 5/1991 | Lemay |
| 5,013,316 A | 5/1991 | Goble et al. |
| 5,019,032 A | 5/1991 | Robertson |
| 5,032,508 A | 7/1991 | Naughton et al. |
| 5,036,867 A | 8/1991 | Biswas |
| 5,053,043 A | 10/1991 | Gottesman et al. |
| 5,085,661 A | 2/1992 | Moss |
| 5,112,344 A | 5/1992 | Petros |
| 5,123,428 A | 6/1992 | Schwarz |
| 5,141,520 A | 8/1992 | Goble et al. |
| 5,149,329 A | 9/1992 | Richardson |
| 5,188,636 A | 2/1993 | Fedotov |
| 5,209,756 A | 5/1993 | Seedhom et al. |
| 5,250,033 A | 10/1993 | Evans et al. |
| 5,256,133 A | 10/1993 | Spitz |
| 5,269,783 A | 12/1993 | Sander |
| 5,281,237 A | 1/1994 | Gimpelson |
| 5,328,077 A | 7/1994 | Lou |
| 5,337,736 A | 8/1994 | Reddy |
| 5,362,294 A | 11/1994 | Seitzinger |
| 5,368,595 A | 11/1994 | Lewis |
| 5,370,650 A | 12/1994 | Tovey et al. |
| 5,370,662 A | 12/1994 | Stone et al. |
| 5,376,097 A | 12/1994 | Phillips |
| 5,383,904 A | 1/1995 | Totakura et al. |
| 5,386,836 A | 2/1995 | Biswas |
| 5,403,328 A | 4/1995 | Shallman |
| 5,413,598 A | 5/1995 | Moreland |
| 5,439,467 A | 8/1995 | Benderev et al. |
| 5,474,518 A | 12/1995 | Velaquez |
| 5,474,543 A | 12/1995 | McKay |
| 5,518,504 A | 5/1996 | Polyak |
| 5,520,700 A | 5/1996 | Beyar et al. |
| 5,520,703 A | 5/1996 | Essig |
| 5,522,820 A | 6/1996 | Caspari et al. |
| 5,527,342 A | 6/1996 | Pietrzak et al. |
| 5,544,664 A | 8/1996 | Benderev et al. |
| 5,562,689 A | 10/1996 | Green et al. |
| 5,571,139 A | 11/1996 | Jenkins, Jr. |
| 5,582,188 A | 12/1996 | Benderev et al. |
| 5,591,163 A | 1/1997 | Thompson |
| 5,591,206 A | 1/1997 | Moufarrege |
| 5,611,515 A | 3/1997 | Benderev et al. |
| 5,628,756 A | 5/1997 | Barker, Jr. et al. |
| 5,633,286 A | 5/1997 | Chen |
| 5,643,320 A | 7/1997 | Lower et al. |
| 5,669,935 A | 9/1997 | Rosenman et al. |
| 5,683,349 A | 11/1997 | Makower et al. |
| 5,697,931 A | 12/1997 | Thompson |
| 5,709,708 A | 1/1998 | Thal |
| 5,725,541 A | 3/1998 | Anspach, III et al. |
| 5,741,282 A | 4/1998 | Anspach, III et al. |
| 5,782,916 A | 7/1998 | Pintauro et al. |
| 5,785,640 A | 7/1998 | Kresch et al. |
| 5,807,403 A | 9/1998 | Beyar et al. |
| 5,836,314 A | 11/1998 | Benderev et al. |
| 5,836,315 A | 11/1998 | Benderev et al. |
| 5,840,011 A | 11/1998 | Landgrebe et al. |
| 5,842,478 A | 12/1998 | Benderev et al. |
| 5,860,425 A | 1/1999 | Benderev et al. |
| 5,899,909 A | 5/1999 | Claren et al. |
| 5,919,232 A | 7/1999 | Chaffringeon et al. |
| 5,922,026 A | 7/1999 | Chin |
| 5,925,047 A | 7/1999 | Errico et al. |
| 5,934,283 A | 8/1999 | Willem et al. |
| 5,935,122 A | 8/1999 | Fourkas et al. |
| 5,944,732 A | 8/1999 | Raulerson et al. |
| 5,954,057 A | 9/1999 | Li |
| 5,972,000 A | 10/1999 | Beyar et al. |
| 5,980,558 A | 11/1999 | Wiley |
| 5,984,927 A | 11/1999 | Wenstrom, Jr. |
| 5,988,171 A | 11/1999 | Sohn et al. |
| 5,997,554 A | 12/1999 | Thompson |
| 6,010,447 A | 1/2000 | Kardjian |
| 6,027,523 A | 2/2000 | Schmieding |
| 6,030,393 A | 2/2000 | Corlew |
| 6,031,148 A | 2/2000 | Hayes et al. |
| 6,036,701 A | 3/2000 | Rosenman |
| 6,039,686 A | 3/2000 | Kovac |
| 6,042,534 A | 3/2000 | Gellman et al. |
| 6,042,536 A | 3/2000 | Tihon et al. |
| 6,042,583 A | 3/2000 | Thompson et al. |
| 6,048,351 A | 4/2000 | Gordon et al. |
| 6,050,937 A | 4/2000 | Benderev |
| 6,053,935 A | 4/2000 | Brenneman et al. |
| 6,056,688 A | 5/2000 | Benderev et al. |
| 6,068,591 A | 5/2000 | Bruckner et al. |
| 6,071,290 A | 6/2000 | Compton |
| 6,074,341 A | 6/2000 | Anderson et al. |
| 6,077,216 A | 6/2000 | Benderev et al. |
| 6,099,538 A | 8/2000 | Moses |
| 6,099,551 A | 8/2000 | Gabbay |
| 6,099,552 A | 8/2000 | Adams |
| 6,106,545 A | 8/2000 | Egan |

(56) References Cited

U.S. PATENT DOCUMENTS

| | | |
|---|---|---|
| 6,110,101 A | 8/2000 | Tihon et al. |
| 6,117,067 A | 9/2000 | Gil-Vernet |
| 6,127,597 A | 10/2000 | Beyar et al. |
| 6,168,611 B1 | 1/2001 | Rizvi |
| 6,183,484 B1 | 2/2001 | Matsutani et al. |
| 6,200,330 B1 | 3/2001 | Benderev et al. |
| 6,221,005 B1 | 4/2001 | Bruckner et al. |
| 6,241,736 B1 | 6/2001 | Sater et al. |
| 6,264,676 B1 | 7/2001 | Gellman et al. |
| 6,273,852 B1 | 8/2001 | Lehe et al. |
| 6,302,840 B1 | 10/2001 | Benderev |
| 6,306,079 B1 | 10/2001 | Trabucco |
| 6,322,492 B1 | 11/2001 | Kovac |
| 6,328,686 B1 | 12/2001 | Kovac |
| 6,328,744 B1 | 12/2001 | Harari et al. |
| 6,334,446 B1 | 1/2002 | Beyar |
| 6,352,553 B1 | 3/2002 | van der Burg et al. |
| 6,382,214 B1 | 5/2002 | Raz et al. |
| 6,387,041 B1 | 5/2002 | Harari et al. |
| 6,406,423 B1 | 6/2002 | Scetbon |
| 6,406,480 B1 | 6/2002 | Beyar et al. |
| 6,414,179 B1 | 7/2002 | Banville |
| 6,423,080 B1 | 7/2002 | Gellman et al. |
| 6,451,024 B1 | 9/2002 | Thompson et al. |
| 6,475,139 B1 | 11/2002 | Miller |
| 6,478,727 B2 | 11/2002 | Scetbon |
| 6,482,214 B1 | 11/2002 | Sidor, Jr. et al. |
| 6,491,703 B1 | 12/2002 | Ulmsten |
| 6,494,906 B1 | 12/2002 | Owens |
| 6,502,578 B2 | 1/2003 | Raz et al. |
| 6,506,190 B1 | 1/2003 | Walshe |
| 6,530,943 B1 | 3/2003 | Hoepffner et al. |
| 6,575,897 B1 | 6/2003 | Ory |
| 6,582,443 B2 | 6/2003 | Cabak et al. |
| 6,592,515 B2 | 7/2003 | Thierfelder |
| 6,592,610 B2 | 7/2003 | Beyar |
| 6,596,001 B2 | 7/2003 | Stormby et al. |
| 6,599,235 B2 | 7/2003 | Kovac |
| 6,599,323 B2 | 7/2003 | Melican et al. |
| 6,602,260 B2 | 8/2003 | Harari et al. |
| 6,612,977 B2 | 9/2003 | Staskin |
| 6,638,210 B2 | 10/2003 | Berger |
| 6,638,211 B2 | 10/2003 | Suslian et al. |
| 6,638,284 B1 | 10/2003 | Rousseau et al. |
| 6,641,524 B2 | 11/2003 | Kovac |
| 6,641,525 B2 | 11/2003 | Rocheleau |
| 6,648,921 B2 | 11/2003 | Anderson |
| 6,652,450 B2 | 11/2003 | Neisz et al. |
| 6,673,010 B2 | 1/2004 | Skiba et al. |
| 6,685,629 B2 | 2/2004 | Therin |
| 6,689,047 B2 | 2/2004 | Gellman et al. |
| 6,691,711 B2 | 2/2004 | Raz |
| 6,699,175 B2 | 3/2004 | Miller |
| 6,702,827 B1 | 3/2004 | Lund |
| 6,752,814 B2 | 6/2004 | Gellman et al. |
| 6,755,781 B2 | 6/2004 | Gellman |
| 6,802,807 B2 | 10/2004 | Anderson |
| 6,830,052 B2 | 12/2004 | Carter et al. |
| 6,881,184 B2 | 4/2005 | Zappala |
| 6,884,212 B2 | 4/2005 | Thierfelder et al. |
| 6,893,448 B2 | 5/2005 | O'Quinn et al. |
| 6,908,425 B2 | 6/2005 | Luscombe |
| 6,908,473 B2 | 6/2005 | Skiba et al. |
| 6,911,002 B2 | 6/2005 | Fierro |
| 6,911,003 B2 | 6/2005 | Anderson et al. |
| 6,932,759 B2 | 8/2005 | Kammerer |
| 6,936,052 B2 | 8/2005 | Gellman et al. |
| 6,936,054 B2 | 8/2005 | Chu |
| 6,953,428 B2 | 10/2005 | Gellman et al. |
| 6,960,160 B2 | 11/2005 | Browning |
| 6,971,986 B2 | 12/2005 | Staskin et al. |
| 6,974,462 B2 | 12/2005 | Sater |
| 6,981,944 B2 | 1/2006 | Jamiolkowski |
| 6,981,983 B1 | 1/2006 | Rosenblatt et al. |
| 6,991,597 B2 | 1/2006 | Gellman et al. |
| 7,014,607 B2 | 3/2006 | Gellman |
| 7,025,063 B2 | 4/2006 | Snitkin |
| 7,025,772 B2 | 4/2006 | Gellman et al. |
| 7,037,255 B2 | 5/2006 | Inman |
| 7,048,682 B2 | 5/2006 | Neisz et al. |
| 7,056,333 B2 | 6/2006 | Walshe |
| 7,070,556 B2 | 7/2006 | Anderson |
| 7,070,558 B2 | 7/2006 | Gellman et al. |
| 7,083,568 B2 | 8/2006 | Neisz et al. |
| 7,083,637 B1 | 8/2006 | Tannhauser |
| 7,087,065 B2 | 8/2006 | Ulmsten et al. |
| 7,112,210 B2 | 9/2006 | Ulmsten et al. |
| 7,121,997 B2 | 10/2006 | Kammerer et al. |
| 7,131,943 B2 | 11/2006 | Kammerer |
| 7,131,944 B2 | 11/2006 | Jacquetin |
| 7,175,591 B2 | 2/2007 | Kaladelfos |
| 7,198,597 B2 | 4/2007 | Siegel et al. |
| 7,226,407 B2 | 6/2007 | Kammerer |
| 7,226,408 B2 | 6/2007 | Harari et al. |
| 7,229,404 B2 | 6/2007 | Bouffier |
| 7,229,453 B2 | 6/2007 | Anderson |
| 7,235,043 B2 | 6/2007 | Gellman et al. |
| 7,261,723 B2 | 8/2007 | Smith et al. |
| 7,297,102 B2 | 11/2007 | Smith et al. |
| 7,299,803 B2 | 11/2007 | Kovac |
| 7,303,525 B2 | 12/2007 | Watschke et al. |
| 7,326,213 B2 | 2/2008 | Benderev et al. |
| 7,347,812 B2 | 3/2008 | Mellier |
| 7,351,197 B2 | 4/2008 | Montpetit et al. |
| 7,357,773 B2 | 4/2008 | Watschke et al. |
| 7,364,541 B2 | 4/2008 | Chu et al. |
| 7,371,245 B2 | 5/2008 | Evans et al. |
| 7,387,634 B2 | 6/2008 | Benderev |
| 7,393,320 B2 | 7/2008 | Montpetit et al. |
| 7,407,480 B2 | 8/2008 | Staskin |
| 7,410,460 B2 | 8/2008 | Benderev |
| 7,413,540 B2 | 8/2008 | Gellman et al. |
| 7,422,557 B2 | 9/2008 | Arnal |
| 7,431,690 B2 | 10/2008 | Bryon et al. |
| 7,494,495 B2 | 2/2009 | Delorme et al. |
| 7,500,945 B2 | 3/2009 | Cox |
| 7,513,865 B2 | 4/2009 | Bourne et al. |
| 7,527,588 B2 | 5/2009 | Zaddem et al. |
| 7,588,598 B2 | 9/2009 | Delorme et al. |
| 7,601,118 B2 | 10/2009 | Smith et al. |
| 7,611,454 B2 | 11/2009 | De Leval |
| 7,621,864 B2 | 11/2009 | Suslian et al. |
| 7,637,860 B2 | 12/2009 | MacLean |
| 7,686,759 B2 | 3/2010 | Sater |
| 7,691,050 B2 | 4/2010 | Gellman et al. |
| 7,722,527 B2 | 5/2010 | Bouchier et al. |
| 7,722,528 B2 | 5/2010 | Arnal et al. |
| 7,740,576 B2 | 6/2010 | Hodroff |
| 7,753,839 B2 | 7/2010 | Siegel et al. |
| 7,762,942 B2 | 7/2010 | Neisz et al. |
| 7,766,926 B2 | 8/2010 | Bosely et al. |
| 7,789,821 B2 | 9/2010 | Browning |
| 7,981,024 B2 | 7/2011 | Levy |
| 8,172,745 B2 | 5/2012 | Rosenblatt |
| 2001/0049467 A1 | 12/2001 | Lehe et al. |
| 2002/0007222 A1 | 1/2002 | Desai |
| 2002/0028980 A1 | 3/2002 | Thierfelder et al. |
| 2002/0128670 A1 | 9/2002 | Ulmsten et al. |
| 2002/0147382 A1 | 10/2002 | Neisz et al. |
| 2002/0151909 A1 | 10/2002 | Gellman et al. |
| 2002/0161382 A1 | 10/2002 | Neisz |
| 2003/0004581 A1 | 1/2003 | Rousseau |
| 2003/0036676 A1 | 2/2003 | Scetbon |
| 2003/0065402 A1 | 4/2003 | Anderson et al. |
| 2003/0176875 A1 | 9/2003 | Anderson |
| 2003/0220658 A1 | 11/2003 | Hatch et al. |
| 2004/0015057 A1 | 1/2004 | Rocheleau et al. |
| 2004/0073235 A1 | 4/2004 | Lund |
| 2004/0138587 A1* | 7/2004 | Lyons, IV ........ A61B 17/00234 600/562 |
| 2004/0225181 A1 | 11/2004 | Chu et al. |
| 2004/0267088 A1 | 12/2004 | Krammerer |
| 2005/0000523 A1 | 1/2005 | Beraud |
| 2005/0004427 A1 | 1/2005 | Cervigni |

(56) References Cited

U.S. PATENT DOCUMENTS

| | | |
|---|---|---|
| 2005/0004576 A1 | 1/2005 | Benderev |
| 2005/0038451 A1 | 2/2005 | Rao et al. |
| 2005/0055104 A1 | 3/2005 | Arnal et al. |
| 2005/0131391 A1 | 6/2005 | Chu et al. |
| 2005/0131393 A1 | 6/2005 | Chu et al. |
| 2005/0199249 A1 | 9/2005 | Karram |
| 2005/0245787 A1 | 11/2005 | Cox et al. |
| 2005/0256530 A1 | 11/2005 | Petros |
| 2005/0277806 A1 | 12/2005 | Cristalli |
| 2005/0278037 A1 | 12/2005 | Delorme et al. |
| 2005/0283189 A1 | 12/2005 | Rosenblatt et al. |
| 2006/0015010 A1 | 1/2006 | Jaffe et al. |
| 2006/0058578 A1 | 3/2006 | Browning |
| 2006/0089524 A1 | 4/2006 | Chu |
| 2006/0089525 A1 | 4/2006 | Mamo et al. |
| 2006/0122457 A1 | 6/2006 | Kovac |
| 2006/0028828 A1 | 7/2006 | Cox et al. |
| 2006/0155307 A1* | 7/2006 | Rosch ............... A61B 17/0469 606/139 |
| 2006/0173237 A1 | 8/2006 | Jacquetin |
| 2006/0195007 A1 | 8/2006 | Anderson |
| 2006/0195011 A1 | 8/2006 | Arnal |
| 2006/0217589 A1 | 9/2006 | Wan et al. |
| 2006/0229493 A1 | 10/2006 | Weiser et al. |
| 2006/0229596 A1 | 10/2006 | Weiser et al. |
| 2006/0252980 A1 | 11/2006 | Arnal et al. |
| 2006/0287571 A1 | 12/2006 | Gozzi |
| 2007/0015953 A1 | 1/2007 | MacLean |
| 2007/0049952 A1* | 3/2007 | Weiss ............... A61B 17/0218 606/144 |
| 2007/0078295 A1 | 4/2007 | Iandgrebe |
| 2007/0173864 A1 | 7/2007 | Chu |
| 2007/0213744 A1* | 9/2007 | Farris ............... A61B 17/0469 606/139 |
| 2007/0260258 A1* | 11/2007 | Sommerich ....... A61B 17/8819 606/92 |
| 2008/039678 A1 | 2/2008 | Montpetit et al. |
| 2008/0097391 A1* | 4/2008 | Feinberg .......... A61B 17/00491 604/523 |
| 2008/0140218 A1 | 6/2008 | Staskin et al. |
| 2008/0300607 A1 | 12/2008 | Meade et al. |
| 2009/0005634 A1 | 1/2009 | Rane |
| 2009/0012353 A1 | 1/2009 | Beyer |
| 2009/0221868 A1 | 9/2009 | Evans |
| 2010/0022822 A1 | 1/2010 | Walshe |
| 2010/0114123 A1 | 5/2010 | Nason |
| 2010/0179575 A1 | 7/2010 | Von Pechmann et al. |
| 2010/0261950 A1 | 10/2010 | Lund |
| 2010/0280627 A1 | 11/2010 | Hanes, II |
| 2010/0305581 A1 | 12/2010 | Hart |
| 2011/0028995 A1* | 2/2011 | Miraki ............... A61B 17/0482 606/144 |
| 2011/0124954 A1 | 5/2011 | Odhahl |
| 2011/0174313 A1 | 7/2011 | Von Pechmann et al. |
| 2012/0016185 A1 | 1/2012 | Sherts et al. |

FOREIGN PATENT DOCUMENTS

| | | |
|---|---|---|
| DE | 2305815 | 2/1973 |
| DE | 4220283 C2 | 5/1994 |
| DE | 19544162 | 4/1997 |
| DE | 10211360 | 9/2003 |
| DE | 20016866 | 3/2007 |
| EP | 0248544 A1 | 12/1987 |
| EP | 0470308 A1 | 2/1992 |
| EP | 0650703 A1 | 6/1994 |
| EP | 0643945 A2 | 7/1994 |
| EP | 0632999 A1 | 1/1995 |
| EP | 1093758 A1 | 4/2001 |
| EP | 1060714 A3 | 9/2002 |
| EP | 1342450 B1 | 9/2003 |
| FR | 2787990 A1 | 7/2000 |
| FR | 2852813 A1 | 1/2004 |
| GB | 2268690 A | 1/1994 |
| GB | 2353220 A | 10/2000 |
| IT | 1299162 | 4/1998 |
| SU | 1225547 A1 | 4/1986 |
| SU | 1342486 A | 10/1987 |
| WO | WO9317635 A1 | 9/1993 |
| WO | WO9319678 A2 | 10/1993 |
| WO | WO9511631 A1 | 5/1995 |
| WO | WO9525469 A1 | 9/1995 |
| WO | WO9716121 A1 | 5/1997 |
| WO | WO9730638 A1 | 8/1997 |
| WO | WO9747244 A1 | 12/1997 |
| WO | WO9819606 A1 | 5/1998 |
| WO | WO9835606 A1 | 8/1998 |
| WO | WO9835616 A1 | 8/1998 |
| WO | WO9835632 A1 | 8/1998 |
| WO | WO9842261 A1 | 10/1998 |
| WO | WO9853746 A1 | 12/1998 |
| WO | WO9916381 A1 | 4/1999 |
| WO | WO9937217 A1 | 7/1999 |
| WO | WO9952450 A1 | 10/1999 |
| WO | WO9953844 A1 | 10/1999 |
| WO | WO1999/059477 | 11/1999 |
| WO | WO9959477 A1 | 11/1999 |
| WO | WO0064370 A1 | 2/2000 |
| WO | WO0013601 A1 | 3/2000 |
| WO | WO0018319 A1 | 4/2000 |
| WO | WO0027304 A1 | 5/2000 |
| WO | WO0040158 A2 | 7/2000 |
| WO | WO00578121 A1 | 10/2000 |
| WO | WO0068030 A1 | 11/2000 |
| WO | WO0074594 A1 | 12/2000 |
| WO | WO0074613 A1 | 12/2000 |
| WO | WO0074633 A2 | 12/2000 |
| WO | WO0106951 A1 | 2/2001 |
| WO | WO0126581 A1 | 4/2001 |
| WO | WO0139670 A1 | 6/2001 |
| WO | WO0145588 A1 | 6/2001 |
| WO | WO0145589 A1 | 6/2001 |
| WO | WO0156499 A1 | 8/2001 |
| WO | WO0228312 A1 | 4/2002 |
| WO | WO0228315 A2 | 4/2002 |
| WO | WO0230293 A1 | 4/2002 |
| WO | WO0232284 A2 | 4/2002 |
| WO | WO0234124 A2 | 5/2002 |
| WO | WO0238079 A2 | 5/2002 |
| WO | WO0239890 A2 | 5/2002 |
| WO | WO02058563 A1 | 8/2002 |
| WO | WO02062237 A1 | 8/2002 |
| WO | WO02069781 | 9/2002 |
| WO | WO02071953 A2 | 9/2002 |
| WO | WO02078552 A1 | 10/2002 |
| WO | WO02089704 A2 | 11/2002 |
| WO | WO03017848 A1 | 3/2003 |
| WO | WO0303778 A1 | 4/2003 |
| WO | WO03028585 A2 | 4/2003 |
| WO | WO03037215 A2 | 5/2003 |
| WO | WO03041613 A1 | 5/2003 |
| WO | WO03047435 A1 | 6/2003 |
| WO | WO03068107 A1 | 8/2003 |
| WO | WO03075792 A1 | 9/2003 |
| WO | WO0309629 A1 | 11/2003 |
| WO | WO03092546 A2 | 11/2003 |
| WO | WO2004012626 A1 | 2/2004 |
| WO | WO2004016196 A2 | 2/2004 |
| WO | WO2004/017862 | 3/2004 |
| WO | WO2004017862 A2 | 3/2004 |
| WO | WO2004034912 A2 | 4/2004 |
| WO | WO2005037132 A2 | 4/2005 |
| WO | WO2005079702 A1 | 9/2005 |
| WO | WO2005122954 A1 | 12/2005 |
| WO | WO2006015031 A2 | 2/2006 |
| WO | WO2006108145 A1 | 10/2006 |
| WO | WO2007011341 A1 | 1/2007 |
| WO | WO2007014241 A1 | 2/2007 |
| WO | WO2007016083 A1 | 2/2007 |
| WO | WO2007027592 A2 | 3/2007 |
| WO | WO2007059199 A2 | 5/2007 |
| WO | WO2007081955 A1 | 7/2007 |
| WO | WO2007097994 | 8/2007 |

(56) References Cited

FOREIGN PATENT DOCUMENTS

| WO | WO2007137226 A2 | 11/2007 |
|---|---|---|
| WO | WO2007146784 A2 | 12/2007 |
| WO | WO2007149348 A2 | 12/2007 |
| WO | WO2007149555 A2 | 12/2007 |
| WO | WO2008057261 A2 | 5/2008 |
| WO | WO2008124056 A1 | 10/2008 |
| WO | WO2009005714 A2 | 1/2009 |
| WO | WO2009017680 A2 | 2/2009 |
| WO | WO2011/082350 | 7/2011 |

OTHER PUBLICATIONS

"Introducing: AlloSling Fascia The *Natural Choice* for Suburethral Sling Procedures", Advertisement from UroMed Corporation (1 page).
"We're staying ahead of the curve" Introducing the IVS Tunneller Device for Tension Free Procedures, Tyco Healthcare, 3 pages (2002).
Advantage A/T™, Surgical Mesh Sling Kit, Boston Scientific, 6 pages (2002).
Albert H. Aldridge, B.S., M.D., F.A.C.S., Transplantation of Fascia for Relief of Urinary Stress Incontinence, American Journal of Obstetrics and Gynecology, V. 44, pp. 398-411, (1948).
AlloSource product literature (11pages).
Amundsen, Cindy L. et al., Anatomical Correction of Vaginal Vault Prolapse by Uterosacral Ligament Fixation in Women Who Also Require a Pubovaginal Sling, The Journal of Urology, vol. 169, pp. 1770-1774, (May 2003).
Araki, Tohru et al., The Loop-Loosening Procedure for Urination Difficulties After Stamey Suspension of the Vesical Neck, The Journal of Urology, vol. 144, pp. 319-323 (Aug. 1990).
Asmussen, M. et.al., Simultaneous Urethro-Cystometry With a New Technique, Scand J Urol Nephrol 10, p. 7-11 (1976).
Beck, Peter R. et al., Treatment of Urinary Stress Incontinence With Anterior Colporthaphy, Obstetrics and Gynecology, vol. 59 (No. 3), pp. 269-274 (Mar. 1982).
Benderev, Theodore V., MD, A Modified Percutaneous Outpatient Bladder Neck Suspension System, Journal of Urology, vol. 152, pp. 2316-2320 (Dec. 1994).
Benderev, Theodore V., MD, Anchor Fixation and Other Modifications of Endoscopic Bladder Neck Suspension, Urology, vol. 40, No. 5, pp. 409-418 (Nov. 1992).
Bergman, Arieh et al., Three Surgical Procedures for Genuine Stress Incontinence: Five-Year Follow-Up of a Prospective Randomized Study, Am J Obstet Gynecol, vol. 173 No. 1, pp. 66-71 (Jul. 1995).
Blaivas, Jerry et al., Pubovaginal Fascial Sling for the Treatment of Complicated Stress Urinary Incontinence, The Journal of Urology, vol. 145, pp. 1214-1218 (Jun. 1991).
Blaivas, Jerry et al., Type III Stress Urinary Incontinence: Importance of Proper Diagnosis and Treatment, Surgical Forum, pp. 473-475, (1984).
Blaivas, Jerry, Commentary: Pubovaginal Sling Procedure, Experience with Pubovaginal Slings, pp. 93-101 (1990).
Boyles, Sarah Hamilton et al., Procedures for Urinary Incontinence in the United States, 1979-1997, Am J Obstet Gynecol, vol. 189, n. 1, pp. 70-75 (Jul. 2003).
Bryans, Fred E., Marlex Gauze Hammock Sling Operation with Cooper's Ligament Attachment in the Management of Recurrent Urinary Stress Incontinence, American Journal of Obstetrics and Gynecology, vol. 133, pp. 292-294 (Feb. 1979).
Burch, John C., Urethrovaginal Fixation to Cooper's Ligament for Correction of Stress Incontinence, Cystocele, and Prolapse, Am. J. Obst. & Gyn, vol. 31, pp. 281-290 (1961).
Capio™ CL—Transvaginal Suture Capturing Device—Transvaginal Suture Fixation to Cooper's Ligament for Sling Procedures, Boston, Scientific, Microvasive®, 8 pages, (2002).
Cervigni, Mauro et al., The Use of Synthetics in the Treatment of Pelvic Organ Prolapse, Voiding Dysfunction and Female Urology, vol. 11, pp. 429-435 (2001).
Choe, Jong M. et al., Gore-Tex Patch Sling: 7 Years Later, Urology, vol. 54, pp. 641-646 (1999).
Comparison of Tissue Reaction of Monofilament and Multifilament Polypropylene Mesh—A Case Report, Tyco Healthcare, United States Surgical, 4 pages (no date).
Cook/Ob Gyn®, Urogynecology, Copyright Cook Urological Inc., pp. 1-36 (1996).
Dargent, D. et al., Insertion of a Suburethral Sling Through the Obturator Membrane in the Treatment of Female Urinary Incontinence, Gynecol Obstet Fertil, vol. 30, pp. 576-582 (2002).
Das, Sakti et al., Laparoscopic Colpo-Suspension, The Journal of Urology, vol. 154, pp. 1119-1121 (Sep. 1995).
Debodinance, Philipp et al., "Tolerance of Synthetic Tissues in Touch With Vaginal Scars Review to the Point of 287 Cases", European Journal of Obstetrics & Gynecology and Reproductive Biology 87 (1999) pp. 23-30.
Decter, Ross M., Use of the Fascial Sling for Neurogenic Incontinence: Lessons Learned, The Journal of Urology, vol. 150, pp. 683-686 (Aug. 1993).
Delancey, John, MD, Structural Support of the Urethra as it Relates to Stress Urinary Incontinence: The Hammock Hypothesis, Am J Obstet Gynecol, vol. 170 No. 6, pp. 1713-1723 (Jun. 1994).
Delorme, Emmanuel, Trans-Obturator Sling: A Minimal Invasive Procedure to Treat Female Stress Urinary Incontinence, Progres en Urologie, vol. 11, pp. 1306-1313 (2001) English Abstract attached.
Diana, et al., Treatment of Vaginal Vault Prolapse With Abdominal Sacral Colpopexy Using Prolene Mesh, American Journal of Surgery, vol. 179, pp. 126-128, (Feb. 2000).
Eglin et al., Transobturator Subvesical Mesh. Tolerance and short-term results of a 103 case continuous series, Gynecologie Obstetrique & Fertilite, vol. 31, Issue 1, pp. 14-19 (Jan. 2003).
Enzelsberger, H. et al., Urodynamic and Radiologic Parameters Before and After Loop Surgery for Recurrent Urinary Stress Incontinence, Acta Obstet Gynecol Scand, 69, pp. 51-54 (1990).
Eriksen, Bjarne C. et al., Long-Term Effectiveness of the Burch Colposuspension in Female Urinary Stress Incontinence, Acta Obstet Gynecol Scand, 69, pp. 45-50 (1990).
Falconer, C. et al., Clinical Outcome and Changes in Connective Tissue Metabolism After Intravaginal Slingplasty in Stress Incontinence Women, International Urogynecology Journal, pp. 133-137 (1966).
Falconer, C. et al., Influence of Different Sling Materials of Connective Tissue Metabolism in Stress Urinary Incontinent Women, International Urogynecology Journal, Supp. 2, pp. S19-S23 (2001).
Farnsworth, B.N., Posterior Intravaginal Slingplasty (Infracoccygeal Sacropexy) for Sever Posthysterectomy Vaginal Vault Prolapse—A Preliminary Report on Efficacy and Safety, Int Urogynecology J, vol. 13, pp. 4-8 (2002).
Farquhar, Cynthia M. et al., Hysterectomy Rates in the United States 1990-1997, Obstetrics & Gynecology, vol. 99, n. 2, pp. 229-234 (Feb. 2002).
Fidela, Marie R. et al., Pelvic Support Defects and Visceral and Sexual Function in Women Treated With Sacrospinous Ligament Suspension and Pelvic Reconstruction, Am J Obstet Gynecol, vol. 175, n. 6 (Dec. 1996).
Flood, C.G. et al., Anterior Colporrhaphy Reinforce With Marlex Mesh for the Treatment of Cystoceles, International Urogynecology Journal, vol. 9, pp. 200-204 (1998).
Gilja, Ivan et al., A Modified Raz Bladder Neck Suspension Operation (Transvaginal Burch), The Journal of Urology, vol. 153, pp. 1455-1457 (May 1995).
Gittes, Ruben F. et al., No-Incision Pubovaginal Suspension for Stress Incontinence, The Journal of Urology, vol. 138 (Sep. 1987).
Guner, et al., Transvaginal Sacrospinous Colpopexy for Marked Uterovaginal and Vault Prolapse, Inter J of Gynec & Obstetrics, vol. 74, pp. 165-170 (2001).
Gynecare TVT Tension-Free Support for Incontinence, The tension-free solution to female Incontinence, Gynecare Worldwide,6 pages, (2002).
Handa, Victoria L, et al, Banked Human Fascia Lata for the Suburethral Sling Procedure: A Preliminary Report, Obstetrics & Gynecology, vol. 88 No. 6, 5 pages (Dec. 1996).

(56) References Cited

OTHER PUBLICATIONS

Heit, Michael et al., Predicting Treatment Choice for Patients With Pelvic Organ Prolapse, Obstetrics & Gynecology, vol. 101, n. 6, pp. 1279-1284 (Jun. 2003).
Henriksson, L. et al., A Urodynamic Evaluation of the Effects of Abdominal Urethrocystopexy and Vaginal Sling Urethroplasty in Women With Stress Incontinence, Am. J. Obstet. Gynecol. vol. 131, No. 1, pp. 77-82 (Mar. 1, 1978).
Hodgkinson, C. Paul et.al., Urinary Stress Incontinence in the Female, Department of Gynecology and Obstetrics, Henry Ford Hospital, vol. 10, No. 5, p. 493-499, (Nov. 1957).
Holschneider, C. H., et al., The Modified Pereyra Procedure in Recurrent Stress Urinary Incontinence: A 15-year Review, Obstetrics & Gynecology, vol. 83, No. 4, pp. 573-578 (Apr. 1994).
Horbach, Nicollette S., et al., Instruments and Methods, A Suburethral Sling Procedure with Polytetrafluoroethylene for the Treatment of Genuine Stress Incontinence in Patients with Low Urethral Closure Pressure, Obstetrics & Gynecology, vol. 71, No. 4, pp. 648-652 (Apr. 1998).
Ingelman-Sunberg, A. et al., Surgical Treatment of Female Urinary Stress Incontinence, Contr. Gynec. Obstet., vol. 10, pp. 51-69 (1983).
Intramesh L.I.F.T. Siliconized polyester, Cousin Biotech, 1 page (no date).
Intramesh® L.I.F.T.® Polypropylene Less Invasive Free Tape, Cousin Biotech, 2 pages (no date).
IVS Tunneller—A UNIVERSAL instrument for anterior and posterior intra-vaginal tape placement, Tyco Healthcare, 4 pages (Aug. 2002).
IVS Tunneller—ein universelles Instrument fur die Intra Vaginal Schlingenplastik, Tyco Healthcare, 4 pages (2001).
IVS Tunneller, AMA (no date) 4 pages.
IVS Tunneller, Australian Medical Design Breakthrough for GSI, mixed incontinence and vault prolapse, AMA Medical Products, 4 pages (no date).
Jeffcoate, T.N.A. et al., The Results of the Aldridge Sling Operation for Stress Incontinence, Journal of Obstetrics and Gynaecology, pp. 36-39 (1956).
Jones, N.H.J. Reay et al., Pelvic Connective Tissue Resilience Decreases With Vaginal Delivery, Menopause and Uterine Prolapse, Br J Surg, vol. 90, n. 4, pp. 466-472 (Apr. 2003).
Julian, Thomas, The Efficacy of Marlex Mesh in the Repair of Sever, Recurrent Vaginal Prolapse of the Anterior Midvaginal Wall, Am J Obstet Gynecol, vol. 175, n. 6, pp. 1472-1475 (Dec. 1996).
Karram, Mickey et al., Patch Procedure: Modified Transvaginal Fascia Lata Sling for Recurrent for Severe Stress Urinary Incontinence, vol. 75, pp. 461-463 (Mar. 1990).
Karram, Mickey M. et al., Chapter 19 Surgical Treatment of Vaginal Vault Prolapse, Urogynecology and Reconstructive Pelvic Surgery, (Walters & Karram eds.) pp. 235-256 (Mosby 1999).
Kersey, J., The Gauze Hammock Sling Operation in the Treatment of Stress Incontintence, British Journal of Obstetrics and Gynaecology, vol. 90, pp. 945-949 (Oct. 1983).
Klutke, Carl et al., The Anatomy of Stress Incontinence: Magnetic Resonance Imaging of the Female Bladder Neck and Urethra, The Journal of Urology, vol. 143, pp. 563-566 (Mar. 1990).
Klutke, John James et al., Transvaginal Bladder Neck Suspension to Cooper's Ligament: A Modified Pereyra Procedure, Obstetrics Gynecology, vol. 88, No. 2, pp. 294-296 (Aug. 1996).
Klutke, John M.D. et al, The promise of tension-free vaginal tape for female SUI, Contemporary Urology, 7 pages (Oct. 2000).
Korda, A. et al., Experience With Silastic Slings for Female Urinary Incontinence, Aust NZ J. Obstet Gynaecol, vol. 29, pp. 150-154 (May 1989).
Kovac, S. Robert, et al, Pubic Bone Suburethral Stabilization Sling for Recurrent Urinary Incontinence, Obstetrics & Gynecology, vol. 89, No. 4, pp. 624-627 (Apr. 1997).
Kovac, S, Robert, et al, Pubic Bone Suburethral Stabilization Sling: A Long Term Cure for SUI?, Contemporary OB/GYN, 10 pages (Feb. 1998).
Kovac, S. Robert, Follow-up of the Pubic Bone Suburethral Stabilization Sling Operation for Recurrent Urinary Incontinence (Kovac Procedure), Journal of Pelvic Surgery, pp. 156-160 (May 1999).
Kovac, Stephen Robert, M.D., Cirriculum Vitae, pp. 1-33 (Jun. 18, 1999).
Leach, Gary E., et al., Female Stress Urinary Incontinence Clinical Guidelines Panel Report on Surgical Management of Female Stress Urinary Incontinence, American Urological Association, vol. 158, pp. 875-880 (Sep. 1997).
Leach, Gary E., MD; Bone Fixation Technique for Transvaginal Needle Suspension, Urology vol. XXXI, No. 5, pp. 388-390 (May 1988).
Lichtenstein, Irving L. et al, The Tension Free Hernioplasty, The American Journal of Surgery, vol. 157 pp. 188-193 (Feb. 1989).
LigiSure Atlas™, Tyco Healthcare, Valleylab®, 2 pages (no date).
Loughlin, Kevin R. et al., Review of an 8-Year Experience With Modifications of Endoscopic Suspension of the Bladder Neck for Female Stress Incontinence, The Journal of Urology, vol. 143, pp. 44-45 (1990).
Luber, Karl M. et al., The Demographics of Pelvic Floor Disorders; Current Observations and Future Projections, Am J Obstet Gynecol, vol. 184, n. 7, pp. 1496-1503 (Jun. 2001).
Mage, Technique Chirurgicale, L'Interpostion D'Un Treillis Synthetique Dans La Cure Par Voie Vaginale Des Prolapsus Genitaux, J Gynecol Obstet Biol Reprod, vol. 28, pp. 825-829 (1999).
Marchionni, Mauro et al., True Incidence of Vaginal Vault Prolapse—Thirteen Years of Experience, Journal of Reproductive Medicine, vol. 44, n. 8, pp. 679-684 (Aug. 199).
Marinkovic, Serge Peter et al., Triple Compartment Prolapse: Sacrocolpopexy With Anterior and Posterior Mesh Extensions, Br J Obstet Gynaecol, vol. 110, pp. 323-326 (Mar. 2003).
Marshall, Victor Fray et al. The Correction of Stress Incontinence by Simple Vesicourethral Suspension, Surgery, Gynecology and Obstetrics, vol. 88, pp. 509-518 (1949).
McGuire, Edward J. et al., Pubovaginal Sling Procedure for Stress Incontinence, The Journal of Urology, vol. 119, pp. 82-84 (Jan. 1978).
McGuire, Edward J. et al., Abdominal Procedures for Stress Incontinence, Urologic Clinics of North America, pp. 285-290, vol. 12, No. 2 (May 1985).
McGuire, Edward J. et al., Experience With Pubovaginal Slings for Urinary Incontinence at The University of Michigan, Journal of Urology, vol. 138, pp. 90-93(1987).
McGuire, Edward J. et al., Abdominal Fascial Slings, Slings, Raz Female Urology, p. 369-375 (1996).
McGuire, Edwared J., M.D., The Sling Procedure for Urinary Stress Incontinence, Profiles in Urology, pp. 3-18.
McGuire™ Suture Buide, The McGuire™ Suture Guide, a single use instrument designed for the placement of a suburethral sling, Bard, 2 pages (2001).
McIndoe, G. A. et al., The Aldridge Sling Procedure in the Treatment of Urinary Stress Incontinence, Aust. N Z Journal of Obstet Gynecology, pp. 238-239 (Aug. 1987).
McKiel, Charles F. Jr., et al, Marshall-Marchetti Procedure Modification, vol. 96, pp. 737-739 (Nov. 1966).
Migliari, Roberto et al., Tension-Free Vaginal Mesh Repair for Anterior Vaginal Wall Prolapse, Eur Urol. vol. 38, pp. 151-155 (Oct. 1999).
Migliari, Roberto et al., Treatment Results Using a Mixed Fiber Mesh in Patients With Grade IV Cystocele, Journal of Urology, vol. 161, pp. 1255-1258 (Apr. 1999).
Mitek Brochure, Therapy of Urinary Stress Incontinence in Women Using Mitek GIII Anchors, By Valenzio C. Mascio, MD.
Moir, J. Chassar et.al., The Gauze-Hammock Operation, The Journal of Obstetrics and Gynaecology of British Commonwealth, vol. 75 No. 1, pp. 1-9 (Jan. 1968).
Morgan, J. E., A Sling Operation, Using Marlex Polypropylene Mesh, for the Treatment of Recurrent Stress Incontinence, Am. J. Obst. & Gynecol, pp. 369-377 (Feb. 1970).
Morgan, J. E. et al., The Marlex Sling Operation for the Treatment of Recurrent Stress Urinary Incontinence: A 16-Year Review, American Obstetrics Gynecology, vol. 151, No. 2, pp. 224-226 (Jan. 1998).

(56) References Cited

OTHER PUBLICATIONS

Morley, George W. et al., Sacrospinous Ligament Fixations for Eversion of the Vagina, Am J Obstet Gyn, vol. 158, n. 4, pp. 872-881 (Apr. 1988).

Narik, G. et.al., A Simplified Sling Operation Suitable for Routine Use, Gynecological and Obstetrical Clinic, University of Vienna, vol. 84, No. 3, p. 400-405, (Aug. 1, 1962).

Natale, F. et al., Tension Free Cystocele Repair (TCR): Long-Term Follow-Up, International Urogynecology Journal, vol. 11, supp. 1, p. S51 (Oct. 2000).

Nichols, David H., The Mersilene Mesh Gauze-Hammock for Severe Urinary Stress Incontinence, Obstetrics and Gynecology, vol. 41, pp. 88-93 (Jan. 1973).

Nicita, Giulio, A New Operation for Genitourinary Prolapse, Journal of Urology, vol. 160, pp. 741-745 (Sep. 1998).

Niknejad, Kathleen et al., Autologous and Synthetic Urethral Slings for Female Incontinence, Urol Clin N Am, vol. 29, pp. 597-611 (2002).

Norris, Jeffery P. et al., Use of Synthetic Material in Sling Surgery: A Minimally Invasive Approach, Journal of Endourology, vol. 10, pp. 227-230 (Jun. 1996).

O'Donnell, Pat, Combined Raz Urethral Suspension and McGuire Pubovaginal Sling for Treatment of Complicated Stress Urinary Incontinence, Journal Arkansas Medical Society, vol. 88, pp. 389-392 (Jan. 1992).

Ostergard, Donald R. et al., Urogynecology and Urodynamics Theory and Practice, pp. 569-579 (1996).

Paraiso et al., Laparoscopic Surgery for Enterocele, Vaginal Apex Prolapse and Rectocele, Int. Urogynecol J, vol. 10, pp. 223-229 (1999).

Parra, R. O., et al, Experience With a Simplified Technique for the Treatment of Female Stress Urinary Incontinence, British Journal of Urology, pp. 615-617 (1990).

Pelosi, Marco Antonio III et al., Pubic Bone Suburethral Stabilization Sling: Laparoscopic Assessment of a Transvaginal Operation for the Treatment of Stress Urinary Incontinence, Journal of Laparoendoscopic & Advanced Surgical Techniques, vol. 9, No. 1 pp. 45-50 (1999).

Pereyra, Armand J. et al, Pubourethral Supports in Perspective: Modified Pereyra Procedure for Urinary Incontinence, Obstetrics and Gynecology, vol. 59, No. 5, pp. 643-648 (May 1982).

Pereyra, Armand J., M.D., F.A.C.S., A Simplified Surgical Procedure for Correction of Stress Incontinence in Women, West.J.Surg., Obst. & Gynec. p. 223-226, (Jul.-Aug. 1959).

Peter E. Papa Petros et al., Cure of Stress Incontinence By Repair of External Anal Sphincter, Acta Obstet Gynecol Scand, vol. 69, Sup 153, p. 75 (1990).

Peter Petros et al., Anchoring the Midurethra Restores Bladder-Neck Anatomy and Continence, The Lancet, vol. 354, pp. 997-998 (Sep. 18, 1999).

Petros, Peter E. Papa et al., An Anatomical Basis for Success and Failure of Female Incontinence Surgery, Scandinavian Journal of Neurourology and Urodynamics, Sup 153. pp. 55-60 (1993).

Petros, Peter E. Papa et al., An Analysis of Rapid Pad Testing and the History for the Diagnosis of Stress Incontinence, Acta Obstet Gynecol Scand, vol. 71, pp. 529-536 (1992).

Petros, Peter E. Papa et al., An Integral Theroy of Female Urinary Incontinence, Acta Obstetricia et Gynecologica Scandinavica, vol. 69 Sup. 153, pp. 7-31 (1990).

Petros, Peter E. Papa et al., Bladder Instability in Women: A Premature Activation of the Micturition Reflex, Scandinavian Journal of Neurourology and Urodynamics, Sup 153 pp. 235-239 (1993).

Petros, Peter E. Papa et al., Cough Transmission Ratio: An Indicator of Suburethral Vaginal Wall Tension Rather Than Urethral Closure, Acta Obstet Gynecol Scand, vol. 69, Sup 153, pp. 37-39 (1990).

Petros, Peter E. Papa et al., Cure of Urge Incontinence by the Combined Intravaginal Sling and Tuck Operation, Acta Obstet Gynecol Scand, vol. 69, Sup 153, pp. 61-62 (1990).

Petros, Peter E. Papa et al., Further Development of the Intravaginal Slingplasty Procedure—IVS III—(With Midline "Tuck"), Scandinavian Journal of Neurourology and Urodynamics, Sup 153, p. 69-71 (1993).

Petros, Peter E. Papa et al., Medium-Term Follow-Up of the Intravaginal Slingplasty Operation Indicates Minimal Deterioration of Urinary Continence With Time, (3 pages) (1999).

Petros, Peter E. Papa et al., Non Stress Non Urge Female Urinary Incontinence—Diagnosis and Cure: A Preliminary Report, Acta Obstet Gynecol Scand, vol. 69, Sup 153, pp. 69-70 (1990).

Petros, Peter E. Papa et al., Part I: Theoretical, Morphological, Radiographical Correlations and Clinical Perspective, Scandinavian Journal of Neurourology and Urodynamics, Sup 153, pp. 5-28 (1993).

Petros, Peter E. Papa et al., Part II: The Biomechanics of Vaginal Tissue and Supporting Ligaments With Special Relevance to the Pathogenesis of Female Urinary Incontinence, Scandinavian Journal of Neurourology and Urodynamics, Sup 153, pp. 29-40 plus cover sheet (1993).

Petros, Peter E. Papa et al., Part III: Surgical Principles Deriving from the Theory, Scandinavian Journal of Neurourology and Urodynamics, Sup 153, pp. 41-52 (1993).

Petros, Peter E. Papa et al., Part IV: Surgical Applications of the Theory—Development of the Intravaginal Sling Pklasty (IVS) Procedure, Scandinavian Journal of Neurourology and Urodynamics, Sup 153, pp. 53-54 (1993).

Petros, Peter E. Papa et al., Pelvic Floor Rehabilitation According to the Integrated Theory of Female Urinary Incontinence, Chapter 7, pp. 249-258 (book chapter).

Petros, Peter E. Papa et al., Pinch Test for Diagnosis of Stress Urinary Incontinence, Acta Obstet Gynecol Scand, vol. 69, Sup 153, pp. 33-35 (1990).

Petros, Peter E. Papa et al., Pregnancy Effects on the Intravaginal Sling Operation, Acta Obstet Gynecol Scand, vol. 69, Sup 153, pp. 77-79 (1990)

Petros, Peter E. Papa et al., The Autogenic Ligament Procedure: A Technique for Planned Formation of an Artificial Neo-Ligament, Acta Obstet Gynecol Scand, vol. 69, Sup 153, pp. 43-51 (1990).

Petros, Peter E. Papa et al., The Combined Intravaginal Sling and Tuck Operation an Ambulatory Procedure for Cure of Stress and Urge Incontinence, Acta Obstet Gynecol Scand, vol. 69, Sup. 153, pp. 53-59 (1990).

Petros, Peter E. Papa et al., The Development of the Intravaginal Slingplasty Procedure: IVS II—(With Bilateral "Tucks"), Scandinavian Journal of Neurology and Urodynamics, Sup 153, pp. 61-67 (1993).

Petros, Peter E. Papa et al., The Free Graft Procedure for Cure of the Tethered Vagina Syndrome, Scandinavian Journal of Neurourology and Urodynamics, Sup 153, pp. 85-87(1993).

Petros, Peter E. Papa et al., The Further Development of the Intravaginal Slingplasty Procedure—IVS IV—(With "Double Breasted" Unattached Vaginal Flap Repair and "Free" Vaginal Tapes), Scandinavian Journal of Neurourology and Urodynamics, Sup 153, pp. 73-75 (1993).

Petros, Peter E. Papa et al., The Further Development of the Intravaginal Slingplasty Procedure—IVS V—(With "Double Breasted" Unattached Vaginal Flap Repair and Permanent Sling)., Scandinavian Journal of Neurourology and Urodynamics, Sup 153, pp. 77-79 (1993).

Petros, Peter E. Papa et al., The Intravaginal Slingplasty Operation, A Minimally Invasive Technique for Cure of Urinary Incontinence in the Female, Aust, NZ J Obstet Gynaecol, vol. 36, n. 4, pp. 453-461 (1996).

Petros, Peter E. Papa et al., The Intravaginal Slingplasty Procedure: IVS VI—Further Development of the "Double Breasted" Vaginal Flap Repair—Attached Flap, Scandinavian Journal of Neurourology and Urodynamics, Sup 153, pp. 81-84 (1993).

Petros, Peter E. Papa et al., The Posterior Fornix Syndrome: A Multiple Symptom Complex of Pelvic Pain and Abnormal Urinary Symptoms Deriving From Laxity in the Posterior Fornix of Vagina, Scandinavian Journal of Neurourology and Urodynamics, Sup 153, pp. 89-93 (1993).

(56) References Cited

OTHER PUBLICATIONS

Petros, Peter E. Papa et al., The Role of a Lax Posterior Vaginal Fornix in the Causation of Stress and Urgency Symptoms: A Preliminary Report, Acta Obstet Gynecol Scand, vol. 69, Sup 153, pp. 71-73 (1990).
Petros, Peter E. Papa et al., The Tethered Vagina Syndrome, Post Surgical Incontinence and I-Plasty Operation for Cure, Acta Obstet Gynecol Scand, vol. 69, Sup 153, pp. 63-67 (1990).
Petros, Peter E. Papa et al., The Tuck Procedure: A Simplified Vaginal Repair for Treatment of Female Urinary Incontinence, Acta Obstet Gynecol Scand, vol. 69, Sup 153, pp. 41-42 (1990).
Petros, Peter E. Papa et al., Urethral Pressure Increase on Effort Originates from Within the Urethra, and Continence from Musculovaginal Closure, Scandinavian Journal of Neurourology and Urodynamincs, pp. 337-350 (1995).
Petros, Peter E. Papa, Development of Generic Models for Ambulatory Vaginal Surgery—Preliminary Report,International Urogynecology Journal, pp. 20-27 (1998).
Petros, Peter E. Papa, New Ambulatory Surgical Methods Using an Anatomical Classification of Urinary Dysfunction Improve Stress, Urge and Abnormal Emptying, Int. Urogynecology Journal Pelvic Floor Dystfunction, vol. 8 (5), pp. 270-278, (1997).
Petros, Peter E. Papa, Vault Prolapse II; Restoration of Dynamic Vaginal Supports by Infraooccygeal Sacropexy, an Axial Day-Case Vaginal Procedure, Int Urogynecol J, vol. 12, pp. 296-303 (2001).
Rackley, Raymond R. et al., Tension-Free Vaginal Tape and Percutaneous Vaginal Tape Sling Procedures, Techniques in Urology, vol. 7, No. 2, pp. 90-100 (2001).
Rackley, Raymond R. M.D., Synthetic Slings: Five Steps for Successful Placement, Urology Times, p. 46,48,49 (Jun. 2000).
Raz, Shlomo, et al., The Raz Bladder Neck Suspension Results in 206 Patients, The Journal of Urology, pp. 845-846 (1992).
Raz, Shlomo, et al., Female Urology, pp. 80-86, 369-398, 435-442 (1996).
Raz, Shlomo, MD, Modified Bladder Neck Suspension for Female Stress Incontinence, Urology, vol. XVII, No. 1, pp. 82-85 (Jan. 1981).
Readjustable REMEEX® system, Neomedic International, 8 pages (no date).
Richardson, David A. et al., Delayed Reaction to the Dacron Buttress Used in Urethropexy, The Journal of Reproductive Medicine, pp. 689-692, vol. 29, No. 9 (Sep. 1984).
Richter, K., Massive Eversion of the Vagina: Pathogenesis, Diagnosis and Therapy of the "True" Prolapse of the Vaginal Stump, Clin obstet gynecol, vol. 25, pp. 897-912 (1982).
Ridley, John H., Appraisal of the Goebell-Frangenheim-Stoeckel Sling Procedure, American Journal Obst & Gynec., vol. 95, No. 5, pp. 741-721 (Jul. 1, 1986).
Roberts, Henry, M.D., Cystourethrography in Women, Deptment of Obstetrics and Gynaecology, University of Liverpool, May 1952, vol. XXXV, No. 293, pp. 253-259.
Sabre™ Bioabsorbable Sling, Generation Now, Mentor, 4 pages (May 2002).
Sabre™ Surgical Procedure, Mentor, 6 pages (Aug. 2002).
Sanz, Luis E. et al., Modification of Abdominal Sacrocolpopexy Using a Suture Anchor System, The Journal of Reproductive Medicine, vol. 48, n. 7, pp. 496-500 (Jul. 2003).
Seim, Arnfinn et al., A Study of Female Urinary Incontinence in General Practice—Demography, Medical History, and Clinical Findings, Scand J Urol Nephrol, vol. 30, pp. 465-472 (1996).
Sergent, F. et al., Prosthetic Restoration of the Pelvic Diaphragm in Genital Urinary Prolapse Surgery: Transobturator and Infacoccygeal Hammock Technique, J Gynecol Obstet Biol Reprod, vol. 32, pp. 120-126 (Apr. 2003).
Sloan W. R. et al., Stress Incontinence of Urine: A Retrospective Study of the Complications and Late Results of Simple Suprapubic Suburethral Fascial Slings, The Journal of Urology, vol. 110, pp. 533-536 (Nov. 1973).
Spencer, Julia R. et al., A Comparison of Endoscopic Suspension of the Vesical Neck With Suprapubic Vesicourethropexy for Treatment of Stress Urinary Incontinence, The Journal of Urology, vol. 137, pp. 411-415 (Mar. 1987).
Stamey, Thomas A., M.D., Endoscopic Suspension of the Vesical Neck for Urinary Incontinence in Females, Ann. Surgery, vol. 192 No. 4, pp. 465-471 (Oct. 1980).
Stanton, Stuart L., Suprapubic Approaches for Stress Incontinence in Women, Journal of American Geriatrics Society, vol. 38, No. 3, pp. 348-351 (Mar. 1990).
Stanton, Stuart, Springer-Veglag, Surgery of Female Incontinence, pp. 105-113 (1986).
Staskin et al., A Comparison of Tensile Strength among Three Preparations of Irradiated and Non-Irradiated Human Fascia Lata Allografts (2 pages).
Staskin, David R. et al., The Gore-Tex Sling Procedure for Female Sphincteric Incontinence: Indications, Technique, and Results, World Journal of Urology, vol. 15, pp. 295-299 (1997).
Studdiford, William E., Transplantation of Abdominal Fascia for the Relief of Urinary Stress Incontinence, American Journal of Obstetrics and Gynecology, pp. 764-775 (1944).
Subak, Leslee L. et al., Cost of Pelvic Organ Prolapse Surgery in the United States, Obstetrics & Gynecology, vol. 98, n. 4, pp. 646-651 (Oct. 2001).
Sullivan, Eugene S. et al., Total Pelvic Mesh Repair a Ten-Year Experience, Dis. Colon Rectum, vol. 44, No. 6, pp. 857-863 (Jun. 2001).
Support™, Sub-Urethral Perineal Retro-Pubic Tensionless Sling, Matrix Medical (Pty) Ltd, (no date), 1 pg.
Swift, S.E., et al., Case-Control Study of Etiologic Factors in the Development of Sever Pelvic Organ Prolapse, Int Urogynecol J, vol. 12, pp. 187-192 (2001).
T-Sling® (Totally Tension-free) Urinary Incontinence Procedure, Herniamesh, 2 pages (no date).
TVT Tension-free Vaginal Tape, Gynecare, Ethicon, Inc., 23 pages (1999).
Ulmsten, U. et al., A Multicenter Study of Tension-Free Vaginal Tape (TVT) for Surgical Treatment of Stress Urinary Incontinence, International Urogynecology Journal, vol. 9, pp. 210-213 (1998).
Ulmsten, U. et al., An Ambulatory Surgical Procedure Under Local Anesthesia for Treatment of Female Urinary Incontinence, International Urogynecology Journal, vol. 7, pp. 81-86 (May 1996).
Ulmsten, U., Female Urinary Incontinence—A Symptom, Not a Urodynamic Disease, Some Theoretical and Practical Aspects of the Diagnosis a Treatment of Female Urinary Incontinence, International Urogynecology Journal, vol. 6, pp. 2-3 (1995).
Ulmsten, Ulf et al., A Three Year Follow Up of Tension Free Vaginal Tape for Surgical Treatment of Female Stress Urinary Incontinence, British Journal of Obstetrics and Gynaecology, vol. 106, pp. 345-350 (1999).
Ulmsten, Ulf et al., Different Biochemical Composition of Connective Tissue in Continent, Acta Obstet Gynecol Scand, pp. 455-457 (1987).
Ulmsten, Ulf et al., Intravaginal Slingplasty (IVS): An Ambulatory Surgical Procedure for Treatment of Female Urinary Incontinence, Scand J Urol Nephrol, vol. 29, pp. 75-82 (1995).
Ulmsten, Ulf et al., The Unstable Female Urethra, Am. J. Obstet. Gynecol., vol. 144 No. 1, pp. 93-97 (Sep. 1, 1982).
UroMed Access Instrument System for the Sub-urethral Sling Procedure Catalog No. 120235, Directions for Use, (3 pages).
Vesica® Percutaneous Bladder Neck Stabilization Kit, A New Approach to Bladder Neck Suspenison, Microvasive® Boston Scientific Corporation, 4 pages (1995).
Vesica® Sling Kits, Simplifying Sling Procedures, Microvasive® Boston Scientific Corporation, 4 pages (1998).
Villet, R. Réponse De R. Viller A L'Article De D. Dargent et al., Gynécolgie Obstétrique & Fertilité, vol. 31, p. 96 (2003).
Visco, Anthony G. et al., Vaginal Mesh Erosion After Abdominal Sacral Colpopexy, Am J Obstet Gynecol, vol. 184, n. 3, pp. 297-302 (297-302).
Walters, Mark D., Percutaneous Suburethral Slings: State of the Art, Presented at the conference of the American Urogynecologic Society, Chicago, 29 pages (Oct. 2001).

(56) References Cited

OTHER PUBLICATIONS

Waxman, Steve et al., Advanced Urologic Surgery for Urinary Incontinence, The Female Patient, pp. 93-100, vol. 21 (Mar. 1996).
Weber, Anne M. et al., Anterior Vaginal Prolapse: Review of Anatomy and Techniques of Surgical Repair, Obstetrics and Gynecology, vol. 89, n. 2, pp. 311-318 (Feb. 1997).
Webster, George D., Female Urinary Incontinence, Urologic Surgery, pp. 665-679.
Webster, George et al., Voiding Dysfunction Following Cystourethropexy: Its Evaluation and Management, The Journal of Urology, vol. 144, pp. 670-673 (Sep. 1990).
Winter, Chester C., Peripubic Urethropexy for Urinary Stress Incontinence in Women, Urology, vol. XX, No. 4, pp. 408-411 (Oct. 1982).
Winters et al., Abdominal Sacral Colpopexy and Abdominal Enterocele Repair in the Management of Vaginal Vault Prolapse, Urology, vol. 56, supp. 6A, pp. 55-63 (2000).
Woodside, Jeffrey R. et al., Suprapubic Endoscopic Vesical Neck Suspension for the Management of Urinary Incontinence in Myelodysplastic Girls, The Journal of Urology, vol. 135, pp. 97-99 (Jan. 1986).
Zacharin, Robert et al., Pulsion Enterocele: Long-Term Results of an Abdominoperineal Technique, Obstetrics & Gynecology, vol. 55 No. 2, pp. 141-148 (Feb. 1980).
Zacharin, Robert, The Suspensory Mechanism of the Female Urethra, Journal of Anatomy, vol. 97, Part 3, pp. 423-427 (1963).
Zimmern, Phillippe E. et al., Four-Corner Bladder Neck Suspension, Vaginal Surgery for the Urologist, vol. 2, No. 1, pp. 29-36 (Apr. 1994).
Le point sur l'incontinence urinaire, Expertise et Practiques en Urologie, No. 3, Dr. Sophie Conquy [Hospital Cochin, Paris], pp. 17-19.
Mouly, Patrick et al., Vaginal Reconstruction of a Complete Vaginal Prolapse: The Trans Obturator Repair, Journal of Urology, vol. 169, p. 183 (Apr. 2003).
Pourdeyhimi, B, Porosity of Surgical Mesh Fabrics: New Technology, J. Biomed. Mater. Res.: Applied Biomaterials, vol. 23, No. A1, pp. 145-152 (1989).
Drutz, H.P. et al., Clinical and Urodynamic Re-Evaluation of Combined Abdominovaginal Marlex Sling Operations for Recurrent Stress Urinary Incontinence, International Urogynecology Journal, vol. 1, pp. 70-73 (1990).
Petros, Papa PE et al., An Integral Theory and Its Method for the Diagnosis and Management of Female Urinary Incontinence, Scandinavian Journal of Urology and Nephrology, Supplement 153: p. 1 (1993).
Horbach, Nicollette, Suburethral Sling Procedures, Genuine Stress Incontinence, Chapter 42, pp. 569-579.
Mentor Porges, Uratape, ICS/IUGA Symp, Jul. 2002.

* cited by examiner

IMPLANTS, TOOLS, AND METHODS FOR TREATMENTS OF PELVIC CONDITIONS

CROSS REFERENCE TO RELATED APPLICATION

This application is a divisional of U.S. application Ser. No. 13/537,612, filed Jun. 29, 2012, which claims the benefit under 35 U.S.C. § 119(e) of U.S. Provisional Patent Application No. 61/503,009, filed Jun. 30, 2011 and titled "Implants, Tools, and Methods for Treatments of Pelvic Conditions", and U.S. Provisional Patent Application No. 61/506,833, filed Jul. 12, 2011, and titled, "Implants, Tools, and Methods for Treatments of Pelvic Conditions," which are incorporated herein by reference in their entirety.

TECHNICAL FIELD

The present invention relates generally to implants, tools, devices, systems, apparatuses, and related methods for treating pelvic conditions including but not limited to incontinence and prolapse conditions in men and women, for example, as can be treated by sacral colpopexy procedures.

BACKGROUND

Pelvic health for men and women is a medical area of increasing importance, at least in part due to an aging population. Examples of common pelvic ailments include incontinence (e.g., urinary or fecal), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Urinary incontinence can be characterized by the loss or diminution in the ability to maintain the urethral sphincter closed as the bladder fills with urine. Male or female stress urinary incontinence (SUI) generally occurs when the patient is physically stressed.

Other pelvic floor disorders include cystocele, rectocele, enterocele, and prolapse such as anal, uterine and vaginal vault prolapse. Pelvic disorders such as these can result from weakness or damage to normal pelvic support systems.

In its severest forms, vaginal vault prolapse can result in the distension of the vaginal apex outside of the vagina, and is often associated with a rectocele, cystocele or enterocele. An enterocele is a vaginal hernia in which the peritoneal sac containing a portion of the small bowel extends into the rectovaginal space. Vaginal vault prolapse and enterocele represent challenging forms of pelvic disorders for surgeons. One known method of repairing vaginal vault prolapse is by suturing to the supraspinous ligament or attaching the vaginal vault through mesh or fascia to the sacrum. In particular, abdominal sacral colpopexy procedures are considered to be particularly effective treatments; however, such procedures can be relatively invasive and are somewhat complicated.

An additional consideration is that many patients suffering from vaginal vault prolapse also require a surgical procedure to correct stress urinary incontinence that is either symptomatic or latent. Unfortunately, in order to correct one or more of these issues, the procedures that are often used involve lengthy surgical procedure times and/or lengthy recovery periods. Some of these treatments include, for example, abdominal sacralcolpopexy (SCP), which may be performed laparoscopically, and transvaginal sacralcolpopexy (TSCP), wherein these procedures are performed using a variety of different instruments, implants, and surgical methods. It is known to repair vaginal vault prolapse by suturing the vaginal vault (e.g., by stitches) to the supraspinous ligament or by attaching the vaginal vault through mesh or fascia to the sacrum.

There is ongoing need to provide physicians with improved methods and associated instruments for treating pelvic conditions including incontinence, vaginal prolapse (e.g., vaginal vault prolapse), and other pelvic organ prolapse conditions, wherein such methods can include those that are minimally invasive, safe, and highly effective.

SUMMARY

Tools, systems, and methods as described herein can be used to treat pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness, hysterectomies, and the like. In accordance with the invention, sacral colpopexy procedures can be performed through an abdominal opening, laparoscopically, or transvaginally, which procedures will require different approaches, each of which can use certain embodiments of devices and/or methods of the invention.

One procedure that can be used to treat vaginal prolapse conditions is sacral colpopexy. An aspect of certain sacral colpopexy procedures is to place a fixation element (e.g., an anchor such as a bone anchor or soft tissue anchor) into tissue of a posterior pelvic region to secure an implant to the tissue. This aspect of the procedure requires a surgeon to place a tissue anchor at a location deep inside a posterior pelvic region.

Surgical tools and procedural improvements are disclosed herein. Certain embodiments of tools and methods are used for attaching sutures, mesh, or other devices to the anatomy, such as for treating incontinence and/or prolapse. Embodiments of the tools can be used for deploying sutures through a retractor and into the peritoneum, for example. This can be useful for a number of different procedures that require suturing in the peritoneal space, such as sacral colpopexy (e.g., for attaching mesh material to the sacral promontory and for closing the peritoneal membrane over the mesh), high uterosacral suspension procedures (e.g., for passing suture through a tissue structure and fixating the suture to that tissue structure), McCall culdoplasty (i.e., a method of supporting the vaginal cuff by attaching the uterosacral and cardinal ligaments to the peritoneal surface with suture material that can be drawn toward the midline to help close off the cul-de-sac), uterosacral suspension procedures, and the like.

In accordance with the invention, a suturing instrument is disclosed, which is designed to allow for a relatively simple procedure for passing a suture through tissue in a tightly confined space. In one embodiment, the suturing instrument provides for semi-automated, one-handed operation, which also provides for improved needle control. In a particular embodiment, the instrument includes a curved needle with a hook tip that is operated by a slider in a handle. Movement of the slider toward and away from a distal end of the instrument causes the needle to pierce and retract from the target tissue in a predetermined sequence, thereby positioning suture material in a desired configuration in the tissue.

A suture passer is also disclosed, in accordance with the invention, which is designed to allow for a relatively simple procedure for passing a suture through tissue in a tightly confined space, such as during the process of performing a sacral colpopexy procedure. The suture passer generally includes a needle that has a hypo tube that allows a suture to be "injected" through the hypo. The needle/hypo can engage with tissue like a traditional needle, and then a suture can be advanced through the needle by using pressurized air or water to force the needle through the hypo. The needle can then be disengaged from the tissue, leaving the suture connected to the tissue.

BRIEF DESCRIPTION OF THE DRAWINGS

The present invention will be further explained with reference to the appended Figures, wherein like structure is referred to by like numerals throughout the several views, and wherein.

DETAILED DESCRIPTION

Pelvic floor disorders include cystocele, rectocele, enterocele, and uterine and vaginal vault prolapse, levator defects, among others, in male and female patients. These disorders typically result from weakness or damage to normal pelvic support systems. The most common etiologies include childbearing, removal of the uterus, connective tissue defects, prolonged heavy physical labor and postmenopausal atrophy.

Vaginal vault prolapse is the distension of the vaginal apex, in some cases to an orientation outside of the vagina. Vaginal vault prolapse is often associated with a rectocele, cystocele or enterocele. It is known to repair vaginal vault prolapse by suturing the vaginal vault (e.g., by stitches) to the supraspinous ligament or by attaching the vaginal vault through mesh or fascia to the sacrum. Many patients suffering from vaginal vault prolapse also require a concurrent or subsequent surgical procedure to correct stress urinary incontinence that is either symptomatic or latent.

In order to place a sling to stabilize or support the bladder neck or urethra, such as for the treatment of incontinence, surgical procedures and devices are often used. There are a variety of different sling procedures, where the slings used for pubovaginal procedures vary widely in the types of material and anchoring methods. In some cases, the sling is placed under the bladder neck and secured via suspension sutures to a point of attachment (e.g., bone) through an abdominal and/or vaginal incision. Examples of sling procedures are disclosed, for example, in U.S. Pat. Nos. 5,112,344; 5,611,515; 5,842,478; 5,860,425; 5,899,909; 6,039,686, 6,042,534 and 6,110,101.

A sacral colpopexy is one procedure used for providing vaginal vault suspension. It may be performed through an abdominal incision, a vaginal incision, or laparoscopically. A sacral colpopexy entails suspension (by use of an implant such as a strip of mesh) of the vaginal cuff to a region of sacral anatomy such as the sacrum (such as may be accomplished using bone screws that are implanted into the sacrum), a nearby sacrospinous ligament, uterosacral ligament, or anterior longitudinal ligament at the sacral promontory. An implant such as a synthetic mesh can be carefully customized or assembled into a special shape by the surgeon. In some sacral colpopexy procedures that also involve a hysterectomy, an implant can alternatively be attached to posterior vaginal tissue that remains after removal of the uterus and cervix, and also to anatomy to support the vaginal tissue at or around the sacrum, such as to uterosacral ligaments or to the sacrum itself (i.e., to a component of the sacral anatomy).

As used herein, the term "anchor" refers to any structure that can connect an implant to tissue of a pelvic region. The tissue may be bone, or a soft tissue such as a muscle, fascia, ligament, tendon, or the like. The anchor may be any known or future-developed structure, or a structure described herein, useful to connect an implant to such tissue, including but not limited to a clamp, a suture, a soft tissue anchor such as a self-fixating tip, a bone anchor, any of the structures described herein to be useful to connect an implant to soft tissue or bone of a pelvic region, or the like.

The suturing instruments described herein are directed to the surgical treatment of a pelvic condition including prolapse (e.g., any form of vaginal prolapse), urinary and fecal incontinence, levator defects, etc., in a male or female patient. To treat such conditions, one or more implants can be implanted in a male or a female, which implants can include a tissue support portion that can be used to support a urethra or other pelvic tissue, along with one or more extension portions (otherwise known as an end portion or arm) attached or attachable to the tissue support portion. An implant may include portions, pieces, or sections that are synthetic or made of biologic material (e.g., porcine, cadaveric, etc.). Extension portions may be a synthetic mesh, for example, such as a polypropylene mesh, a suture, a biodegradable suture, etc. The tissue support portion may be synthetic (e.g., a polypropylene mesh) or biologic. Examples of implant products that may be similar to those useful according to the present description, include those sold commercially by American Medical Systems, Inc., of Minnetonka Minn., under the trade names "Apogee", "Perigee", and "Elevate" for use in treating pelvic prolapse (including vaginal vault prolapse, cystocele, enterocele, etc.), and under the trade names "Sparc", "Bioarc", "Monarc", "MiniArc", "InVance", and "AdVance" for treating urinary incontinence.

Implants as described can include a tissue fastener at one or both of its ends and can be sutured in one or more additional locations, such as by directly suturing mesh to a target tissue location. A tissue fastener at a distal end or portion of an extension portion can be any of various types, including: a self-fixating tip that is inserted into soft tissue and frictionally retained; soft tissue anchors; biologic adhesive; a soft tissue clamp that can generally include opposing, optionally biased, jaws that close to grab tissue; and opposing male and female connector elements that engage to secure an end of an extension portion to tissue. (See International Patent Application No. PCT/US2007/014120; U.S. patent application Ser. Nos. 12/223,846 and 12/669,099; and WO 2009/075800, the entireties of which are all incorporated herein by reference). An implant may also have one or more extension portions that do not include a tissue fastener, such as may be used if the distal end is designed to be secured to tissue by other methods (e.g., suturing), or is intended to pass through an obturator foramen and a tissue path around a pubic ramus bone, in which case the extension portion may optionally include a connector, dilator, or dilating connector, which connects to an elongate tool that can be used to either push or pull the connector, dilator, or dilating connector through a tissue path (e.g., to a medial incision).

According to various systems as described, one or more suturing instruments may be incorporated or used with an implant or method as described. Examples of useful tools include those that are illustrated in FIGS. 1-4, wherein like structure is generally described with like reference numbers and/or terms. In particular, a suturing instrument 10 is illustrated, which can be used for vaginal vault suspension and attachment of sutures and/or associated implants to the sacral promontory, for example. The instrument can be used for attaching sutures, mesh, or other devices to treat incontinence, prolapse, and/or other pelvic disorders, such as for treating pelvic conditions (e.g., a sacral colpopexy performed transvaginally, laparoscopically, or abdominally). Suturing instrument 10 generally includes a distal end 12, a proximal end 14, a slider rod 16, a connecting rod 18, and a handle 20 at the proximal end 14. The handle 20 further includes a slider or slider mechanism 22 that is located at a proximal end of the slider rod 16 and connecting rod 18. Slider mechanism 22 is moveable in an axial direction (e.g., toward and away from the distal end 12, along a longitudinal axis of the instrument 10) during the suturing process.

Figure 1:
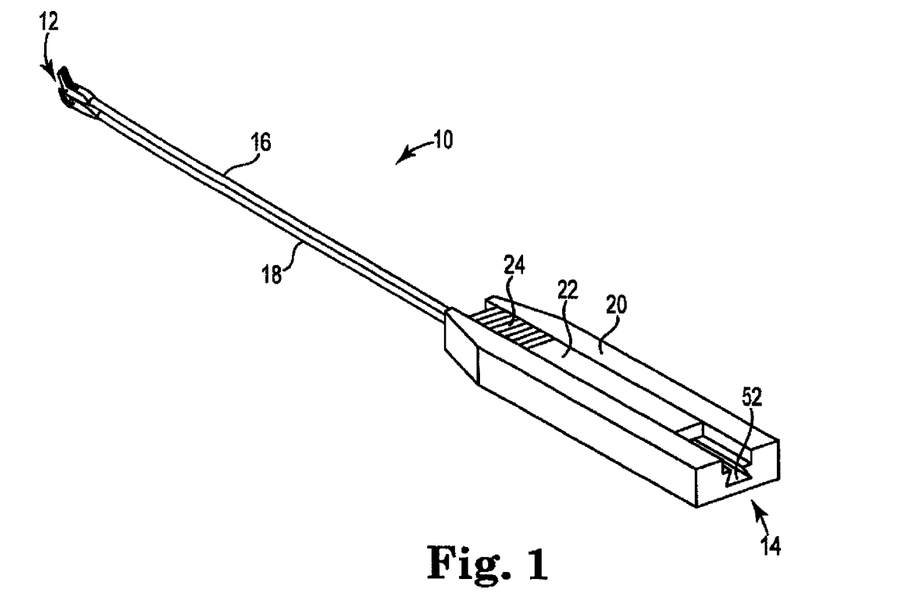
FIG. 1 is a perspective view of an embodiment of a suturing instrument, in accordance with the invention.

Slider mechanism 22 may further include an upper contoured surface 24 or other surface treatment that provides for friction between the user's finger and the surface of the slider mechanism 22. Such a surface 24 may be provided with ridges, as shown, or can instead include a rough or textured surface, which can provide for more controlled movement of the slider relative to the handle, particularly when the user's hand is covered with a surgical glove, for example.

Connecting rod 18 includes a base member 30 extending from its distal end, which may be adhered, friction fit, or otherwise mounted to the connecting rod 18. A needle 32 is connected to the base member 30 about a hinge point 36, as can best be seen in FIG. 2. The needle 32 can have a number of different configurations, such as a curved shaft 37 with flared head member 38 that extends radially outward relative to the outer surface of the shaft 37, as shown, or the needle 32 can instead have a different configuration than illustrated, such as a shaft that is more straight or curved than shown and/or a head portion that is configured differently than shown. In any case, it is desirable for the needle 32 to have a distal needle tip 34 that is sufficiently sharp that it can pierce through a ligament or other tissue structure in a similar manner as other standard needles associated with sutures can penetrate such a ligament or tissue structure.

Slider rod 16 includes a base member 40 extending from its distal end, which may be adhered, friction fit, or otherwise mounted to the slider rod 16. First and second extending arms 42, 44 extend from a distal end of the base member 40 and are spaced from each by the width of a gap 50 that extends in a direction of the width of the base member 40. Extending arms 42, 44 each have a distal aperture 46, 48, respectively, which are adjacent to their distal ends. The arms 42, 44 preferably extend from the base member 40 at an angle relative to the longitudinal axis of the suturing instrument 10, as shown, although it is understood that the angle can be greater or smaller than shown. In addition, it is contemplated that the extension angle can be different for each of the arms 42, 44. In any case, the configuration of the arms 42, 44 can be selected or designed to allow the needle 32 to engage with suture material in a manner in accordance with the present invention, wherein one such method is described below. That is, the illustrated configuration of the arms 42, 44 is only one representative configuration of these arms, wherein it is understood that the functional capability of the arms can be accomplished with a number of different configurations.

With this embodiment, suturing instrument 10 is essentially provided as a four-bar linkage that includes the curved needle 32 that is integrated into a crank, wherein the axis of the crank is mounted at the end of a shaft. The other end of the shaft is mounted to a slider in the handle, and the connecting rod connects the crank to the body of the handle. The needle/crank is caused to rotate by movement of the slider relative to the handle, which can be facilitated via a shaft (not visible) extending between hinge point 36 and crank attachment point 54.

In one embodiment of the suturing instrument 10, the proximal end of the instrument (e.g., the handle 20) extends from the proximal end of the slider rod 16 and connecting rod 18, wherein the length of the rods 16, 18 is sufficient to allow a user to grasp and manipulate the proximal end (e.g., at the handle) as the instrument is extended through an incision or opening (e.g., through a vaginal or abdominal incision) to place the distal end of the rods 16, 18 generally at a location of a posterior pelvic region, (e.g., to place the distal shaft end at a location for placing an anchor at a component of sacral anatomy, such as an anterior longitudinal ligament at a sacral promontory). The connecting rod 18 has a longitudinal axis, and the slider rod 16 similarly has a longitudinal axis. The axes of the connecting rod 18 and slider rod 16 of a particular suturing instrument 10 can be generally parallel to each other, as shown, or can be at least slightly offset relative to each other.

Figure 2:
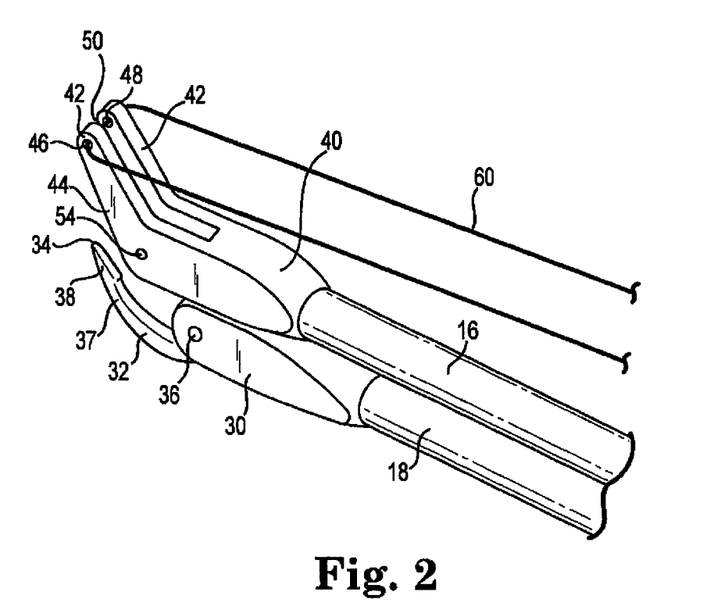
FIG. 2 is a perspective view of the distal end of the suturing instrument of FIG. 1, with a suture and instrument components in a first position.

The suturing instruments of the invention allow for a relatively simple manner of passing a suture through tissue in confined locations, such as can be encountered when maneuvering the device for a sacral colpopexy procedure, for example. In one method of the invention, the needle 32 is positioned as illustrated in FIG. 2, with the slider rod 16 in a forward or distal position. A piece of suture material 60 is passed through the apertures 46, 48 of the extending arms 44, 42, respectively, and the loose ends of the suture 60 can be pulled back toward the proximal end of the instrument 10. At this point, the needle 32 will be spaced from a bottom surface of the arms 42, 44 and from the bottom of gap 50 so that the sharp distal needle tip 34 is exposed. In this position, the needle 32 can be considered to be facing in a generally "forward" direction, where it is available to contact and penetrate tissue.

Figure 3:
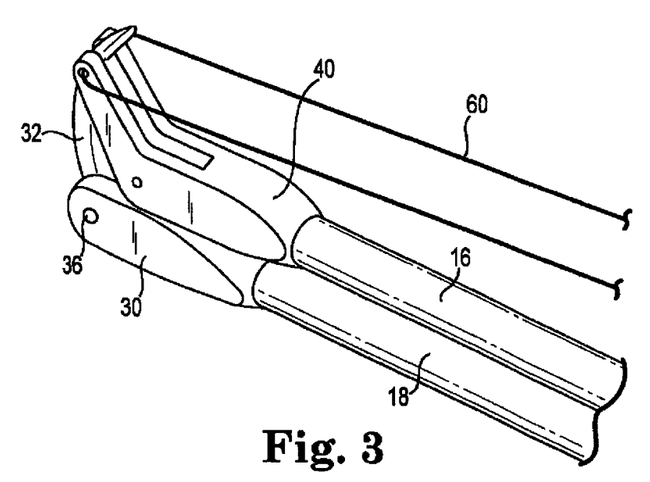
FIG. 3 is a perspective view of the distal end of the suturing instrument of FIG. 1, with a suture and instrument components in a second position.

In another step of the suturing process, the needle 32 can then be rotated about the hinge point 36 by moving the slider 22 relative to the handle 20 (e.g., with the thumb). This movement of the needle 32 about the hinge point 36 will move the needle tip 34 toward the gap 50 between the extending arms 42, 44, as is illustrated in FIG. 3. When the instrument 10 is positioned in this way relative to a target tissue, movement of the slider 22 relative to a distal end 12 of the instrument 10 will cause the needle 32 to arc around the backside of a membrane or target tissue to pierce or penetrate the tissue in a first location. The needle 32 will then continue along this path until it emerges from the front of the target tissue at a second location and until it is positioned in the gap 50 between the extending arms 42, 44 of the base member 40 and adjacent to a portion of the suture that extends across that gap 50. The flared head member 38 can then engage or capture the piece of suture material that is extending across the gap 50 between the arms 42, 44. That is, when the needle 32 includes a flared portion as shown in the figures, the suture 60 can be captured by or engaged (i.e., "hooked") with the flared head member 38 of the needle 32, although it is understood that the needle 32 can have a different end configuration that also facilitates engagement between a portion of needle and the suture material 60 at this point in the suturing process, such as other contoured needle configurations.

Figure 4:
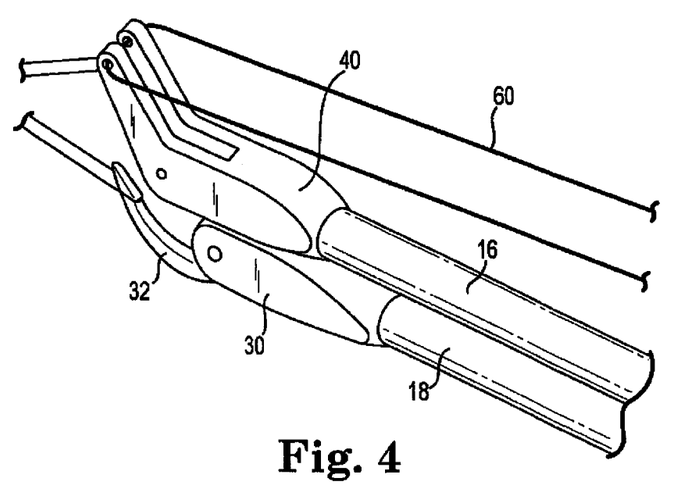
FIG. 4 is a perspective view of the distal end of the suturing instrument of FIG. 1, with a suture and instrument components in a third position.

After the suture 60 is engaged with the tip area of the needle 32, the slider 22 can then be moved in the opposite direction to cause the needle 32 rotate back toward the position illustrated in FIG. 2. In this way, the loop of suture material 60 is pulled backwards through both of the holes that were pierced by the needle during the first steps of the operation, so that the suture is generally positioned as is illustrated in FIG. 4. The suturing instrument 10 can then be withdrawn from the surgical site, pulling the loop of suture material along with it. In this way, a surgeon will have control of the two free ends of suture material that extend through the target tissue, along with the looped end of suture that has been pulled through the tissue.

In one embodiment, the slider 22 is configured to slide within an elongated slot or groove 52 of the handle 20, and also to lock within the groove 52 with a dovetail type of connection, as is illustrated in FIG. 1. In this way, the slider 22 can be assembled to the handle 20 by simply sliding it into the proximal end of the groove 52. If desired, the slider 22 can be prevented from becoming disassembled from the handle by placing a blocking component at its proximal end, such as a cap. In addition, while the slider 22 is illustrated as being a generally rectangular block with a generally planar face that is generally coplanar with the adjacent surfaces of the handle 20, the slider 22 can be configured differently, if desired. For example, the slider 22 can be raised relative to the surface of the handle 20, or can instead be recessed relative to the surface of the handle 20. In yet another alternative, the slider 22 can be replaced with a different type of device that can cause the needle 32 to be activated, such as a rotating knob or other feature that is operatively connected to the needle 32 to provide movement of the needle 32 in the manner illustrated and described herein.

Figure 5:
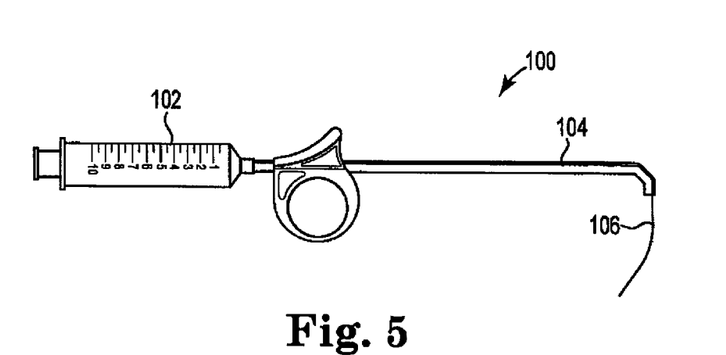
FIG. 5 is a side view of an embodiment of a suture passer, in accordance with the invention.

FIGS. 5-8 illustrate exemplary embodiments of the invention that include suture passers that allow for a relatively simple manner of passing a suture through tissue in confined locations, such as can be encountered during a sacral colpopexy procedure (e.g., transvaginal, laparoscopic, or abdominal sacral colpopexy). As is illustrated in FIG. 5, a suture passer 100 is illustrated, which generally includes a hypotube 104 that extends from a syringe 102. Syringe 102 contains a length of suture material 106, a distal end of which is shown as extending from an end of the hypotube 104. This suture material 106 can be forced from the tube 104 by pressure created in the hypotube 104 that pushes the suture material 106 from the distal end of the tube 104, for example.

Figure 6:
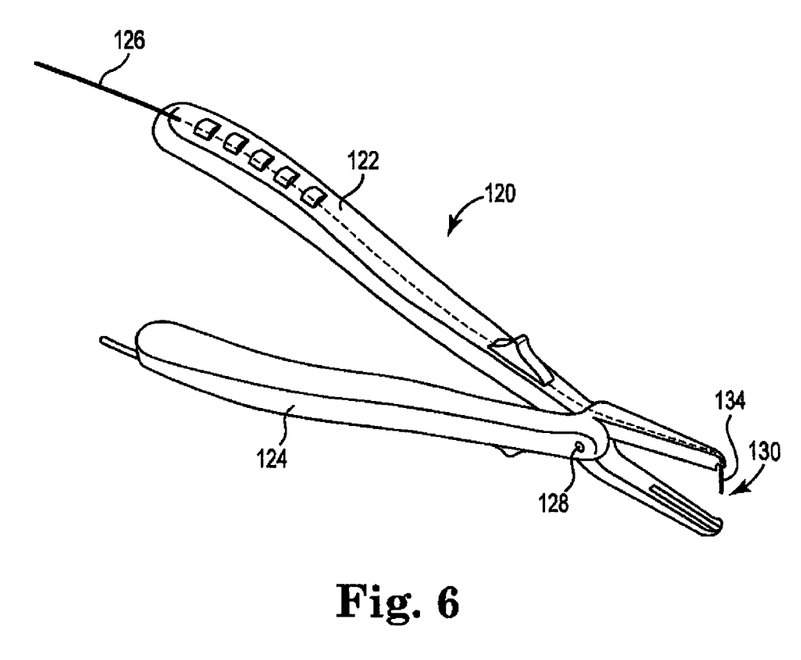
FIG. 6 is a perspective view of an embodiment of a suture passer in accordance with the invention, with a suture and suture passer components in a first position.
Figure 7:
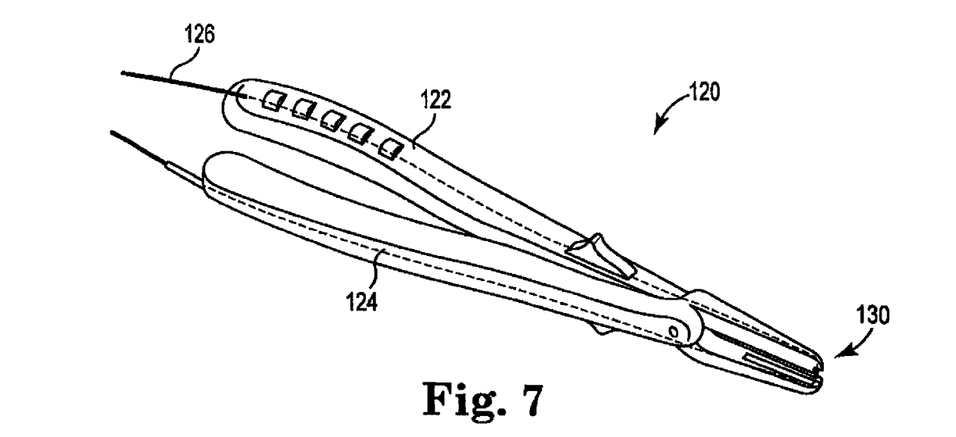
FIG. 7 is a perspective view of the suture passer of FIG. 6, with a suture and suture passer components in a second position.
Figure 8:
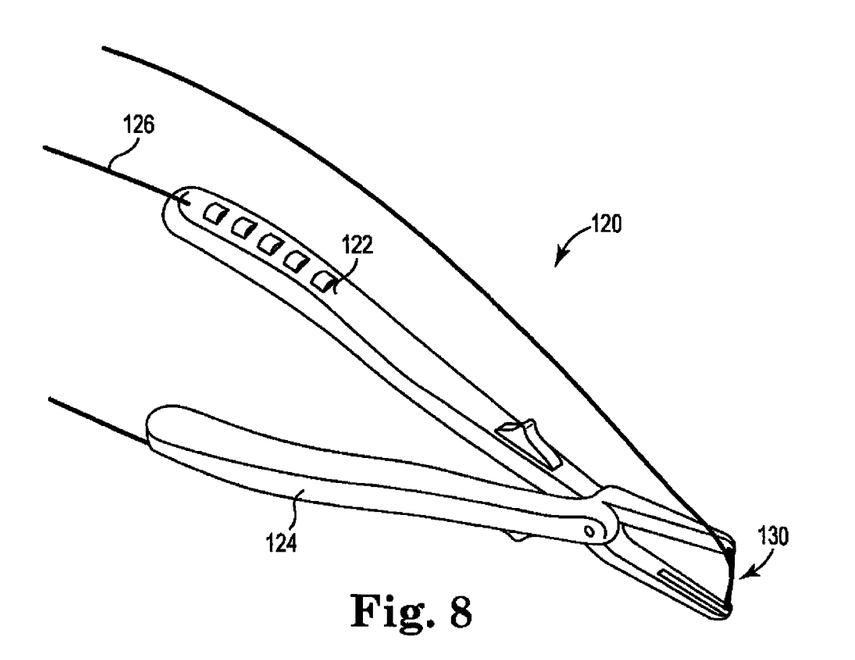
FIG. 8 is a perspective view of the suture passer of FIG. 6, with a suture and suture passer components in a third position.

FIGS. 6-8 illustrate another embodiment of a suture passer 120, which includes two arms 122, 124 at a proximal end of the passer that are moveable relative to each other about a hinge 128, which causes a corresponding movement of components at a distal end 130 of the passer. Each of the arms 122, 124 contains or is associated with a tube that can transport pressurized air, water, or other fluid through its length. As with the embodiment of FIG. 5, the suture passer 120 operates by pressurizing a substance, such as water, and pushing it through a tube, such as a hydrotube.

When a suture material 126 is loaded or otherwise positioned relative to a hydrotube of suture passer 120, the force of the pressurized substance will push the suture material through the length of that tube. Suture material 126 can thereby be transported from the proximal end of suture passer 120 to the distal end 130 of the passer, such as can be facilitated by friction between pressurized water and the suture that pushes the suture material through the tube, for example. In one embodiment, the pressure is high enough that the suture material is then forced through the target tissue in the patient, thereby replacing the function of a needle or other similar component. The suture can then be grasped or otherwise manipulated relative to its location in the patient, and then the suture passer can be pulled from the patient and/or used for additional suturing procedures. In order to operate in this manner, the area of the tube that is in contact with the tissue (e.g., at the distal end 130) can be hollow with relatively sharp ends that can puncture the tissue or otherwise maintain the passer in its desired location relative to the tissue.

With continued reference to FIGS. 6-8, the distal end of arm 124 includes an extending member 134, which may be a needle, a tube, or another thin structure. The distal end of the arm 122 can include a corresponding extending member, such as a member that can engage with the extending member 134, or can include an aperture that can cooperate with the extending member 134 of arm 124. In any case, the arms 122, 124 can be manipulated relative to each other about the hinge 128 to bring the extending member at the distal end 130 in contact with a corresponding feature of the arm 122 (e.g., aperture, tube, or another feature) during the suturing process, as is illustrated in FIG. 8, for example. In this way, the suture can be moved through one of the arms 122, 124, through one of the tips at the distal end 130 of the passer, and through the desired tissue location. The suture can then be captured by an opposing surface at the distal end 130, and then the suture can be pulled through the tissue and additional suturing operations can be performed, if desired.

Suturing instruments described herein can thereby be used for securing implants that are capable of supporting pelvic tissue, and can therefore be useful in conjunction with numerous methods of treating pelvic conditions, such as treating a levator hiatus, anal incontinence, etc. The implants and tools described herein can be made of conventional materials. For example, the various mesh members and portions can be constructed of polymer materials, such as a thin film or sheet material of polypropylene, polyethylene, fluoropolymers or like compatible materials, both permanent and absorbable, and the suturing instrument components can be made of standard surgical-grade materials, such as polymeric materials, stainless steel, and the like.

The disclosed systems, their various components, structures, features, materials and methods may have a number of suitable configurations as shown and described in the previously-incorporated references. Various methods and tools for introducing, deploying, anchoring and manipulate device, implants, and the like as disclosed in the references incorporated herein are envisioned for use with the present invention as well.

All patents, patent applications, and publications cited herein are hereby incorporated by reference in their entirety as if individually incorporated, and include those references incorporated within the identified patents, patent applications and publications.

The invention claimed is:

1. An apparatus comprising:
   a first arm having an extending member, the first arm including a tube defining a lumen and configured to receive a length of a suture material, the lumen configured to receive a pressurized fluid that travels from a first end portion of the tube of the first arm to a second end portion of the tube of the first arm; and
   a second arm defining an aperture, the second arm being rotatably coupled to the first arm and being configured to rotate with respect to the first arm, the second arm including a tube defining a lumen and configured to receive a length of a suture material, the lumen configured to receive a pressurized fluid that travels from a first end portion of the tube of the second arm to a second end portion of the tube of the second arm,
   wherein the aperture of the second arm is configured to receive at least a portion of the extending member of the first arm.

2. The apparatus of claim 1, further comprising a fluid source for pressurizing the fluid.

3. The apparatus of claim 2, wherein the fluid source comprises one of pressurized air and pressurized water.

4. The apparatus of claim 1, wherein the aperture is disposed in a distal end portion of the second arm, the aperture is configured to be sized to receive the suture material of the first arm.

* * * * *